(12) United States Patent
Fox et al.

(10) Patent No.: US 10,835,256 B2
(45) Date of Patent: Nov. 17, 2020

(54) CIRCULAR STAPLING INSTRUMENT WITH FIRING TRIGGER HAVING INTEGRAL RESILIENT FEATURES

(71) Applicant: ETHICON LLC, Guaynabo, PR (US)

(72) Inventors: William D. Fox, New Richmond, OH (US); Gregory J. Bakos, Mason, OH (US)

(73) Assignee: Ethicon LLC, Guaynabo, PR (US)

(*) Notice: Subject to any disclaimer, the term of this patent is extended or adjusted under 35 U.S.C. 154(b) by 169 days.

(21) Appl. No.: 15/717,270

(22) Filed: Sep. 27, 2017

(65) Prior Publication Data

US 2019/0090874 A1    Mar. 28, 2019

(51) Int. Cl.
*A61B 17/115* (2006.01)
*A61B 17/072* (2006.01)
(Continued)

(52) U.S. Cl.
CPC ........ *A61B 17/1155* (2013.01); *A61B 17/072* (2013.01); *A61B 17/07207* (2013.01);
(Continued)

(58) Field of Classification Search
CPC .. A61B 2017/00477; A61B 2017/2923; A61B 2017/00464; A61B 17/0727;
(Continued)

(56) References Cited

U.S. PATENT DOCUMENTS

| | | | |
|---|---|---|---|
| 5,205,459 A | | 4/1993 | Brinkerhoff et al. |
| 5,253,793 A | * | 10/1993 | Green ............. A61B 17/07207 |
| | | | 227/178.1 |

(Continued)

FOREIGN PATENT DOCUMENTS

| | | |
|---|---|---|
| EP | 2 851 012 A1 | 3/2015 |
| WO | WO 2015/065482 A1 | 5/2015 |

(Continued)

OTHER PUBLICATIONS

European Search Report and Written Opinion dated Dec. 19, 2018 for Application No. EP 18196914.8, 7 pgs.

(Continued)

*Primary Examiner* — Hemant Desai
*Assistant Examiner* — Jacob A Smith
(74) *Attorney, Agent, or Firm* — Frost Brown Todd LLC

(57) ABSTRACT

An apparatus includes a body assembly, an end effector, and a firing assembly. The body includes a handle portion and a shaft portion. The end effector includes a staple driver. The firing assembly includes a driver actuator and a trigger. The driver actuator is configured to actuate the staple driver. The driver actuator is slidably housed within the shaft portion. The trigger includes a lever and an integral spring member. The lever is pivotally coupled to the handle portion via a pivot boss of the handle portion. The trigger is configured to pivot between a first position and a second position to slide the driver actuator within the shaft portion, to thereby actuate the staple driver. The integral spring member is at least partially housed within a spring channel of the handle portion and is configured to resiliently bias the trigger toward the first position.

20 Claims, 23 Drawing Sheets

(51) Int. Cl.
*A61B 17/29* (2006.01)
*A61B 17/11* (2006.01)
*A61B 17/28* (2006.01)
*A61B 90/00* (2016.01)

(52) U.S. Cl.
CPC ....... *A61B 17/2909* (2013.01); *A61B 17/1114* (2013.01); *A61B 2017/07257* (2013.01); *A61B 2017/07278* (2013.01); *A61B 2017/1157* (2013.01); *A61B 2017/2845* (2013.01); *A61B 2090/0811* (2016.02)

(58) Field of Classification Search
CPC .............. A61B 17/072; A61B 17/1157; A61B 2017/07257; A61B 2017/2845
USPC ..................... 227/175.1, 175.2, 175.3, 175.4
See application file for complete search history.

(56) References Cited

U.S. PATENT DOCUMENTS

| | | | |
|---|---|---|---|
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A * | 9/1994 | Main .................... | A61B 17/115 227/179.1 |
| 5,533,661 A | 7/1996 | Main et al. | |
| 5,630,540 A * | 5/1997 | Blewett ............ | A61B 17/07207 227/176.1 |
| 6,187,026 B1 * | 2/2001 | Devlin ................ | A61B 17/2909 606/205 |
| 6,250,532 B1 * | 6/2001 | Green .............. | A61B 17/07207 227/175.1 |
| 7,168,604 B2 * | 1/2007 | Milliman ............ | A61B 17/1114 227/175.1 |
| 7,794,475 B2 | 9/2010 | Hess et al. | |
| 7,959,050 B2 * | 6/2011 | Smith ................ | A61B 17/1155 227/175.2 |
| 8,672,207 B2 * | 3/2014 | Shelton, IV ....... | A61B 17/1155 227/179.1 |
| 8,910,847 B2 | 12/2014 | Nalagatla et al. | |
| 9,289,207 B2 | 3/2016 | Shelton, IV | |
| 9,498,222 B2 | 11/2016 | Scheib et al. | |
| 9,532,783 B2 | 1/2017 | Swayze et al. | |
| 9,572,573 B2 | 2/2017 | Scheib et al. | |
| 9,597,081 B2 | 3/2017 | Swayze et al. | |
| 9,724,100 B2 | 8/2017 | Scheib et al. | |
| 2006/0097025 A1 * | 5/2006 | Milliman ............. | A61B 17/115 227/175.1 |
| 2009/0173767 A1 * | 7/2009 | Milliman ............. | A61B 17/115 227/179.1 |
| 2010/0059571 A1 * | 3/2010 | Chen .................... | A61B 17/115 227/175.2 |
| 2011/0261666 A1 | 10/2011 | Vlutters et al. | |
| 2012/0061448 A1 * | 3/2012 | Zingman ............. | A61B 17/072 227/175.2 |
| 2012/0292372 A1 | 11/2012 | Nalagatla et al. | |
| 2012/0292373 A1 | 11/2012 | Nalagatla et al. | |
| 2013/0175315 A1 * | 7/2013 | Milliman ........... | A61B 17/1155 227/175.1 |
| 2013/0284792 A1 * | 10/2013 | Ma ..................... | A61B 1/00087 227/176.1 |
| 2014/0158747 A1 | 6/2014 | Measamer et al. | |
| 2014/0166718 A1 * | 6/2014 | Swayze ............. | A61B 17/1155 227/175.1 |
| 2015/0051640 A1 * | 2/2015 | Twomey ............. | A61B 17/2833 606/208 |
| 2015/0083773 A1 * | 3/2015 | Measamer ........... | A61B 17/068 227/175.1 |
| 2015/0083774 A1 * | 3/2015 | Measamer ........... | A61B 17/068 227/175.1 |
| 2016/0249920 A1 * | 9/2016 | Gupta .................. | A61B 17/072 227/180.1 |
| 2016/0262756 A1 * | 9/2016 | Patankar ........... | A61B 17/07207 |
| 2016/0374671 A1 | 12/2016 | Measamer et al. | |
| 2016/0374684 A1 | 12/2016 | Dinardo et al. | |
| 2017/0105736 A1 * | 4/2017 | Chen .................. | A61B 17/1155 |

FOREIGN PATENT DOCUMENTS

| | | | | |
|---|---|---|---|---|
| WO | WO 2016/046010 A1 | 3/2016 | | |
| WO | WO-2016046010 A1 * | 3/2016 | ........... | A61B 7/1611 |

OTHER PUBLICATIONS

International Search Report and Written Opinion dated Dec. 19, 2018 for Application No. PCT/IB2018/057309, 9 pgs.

* cited by examiner

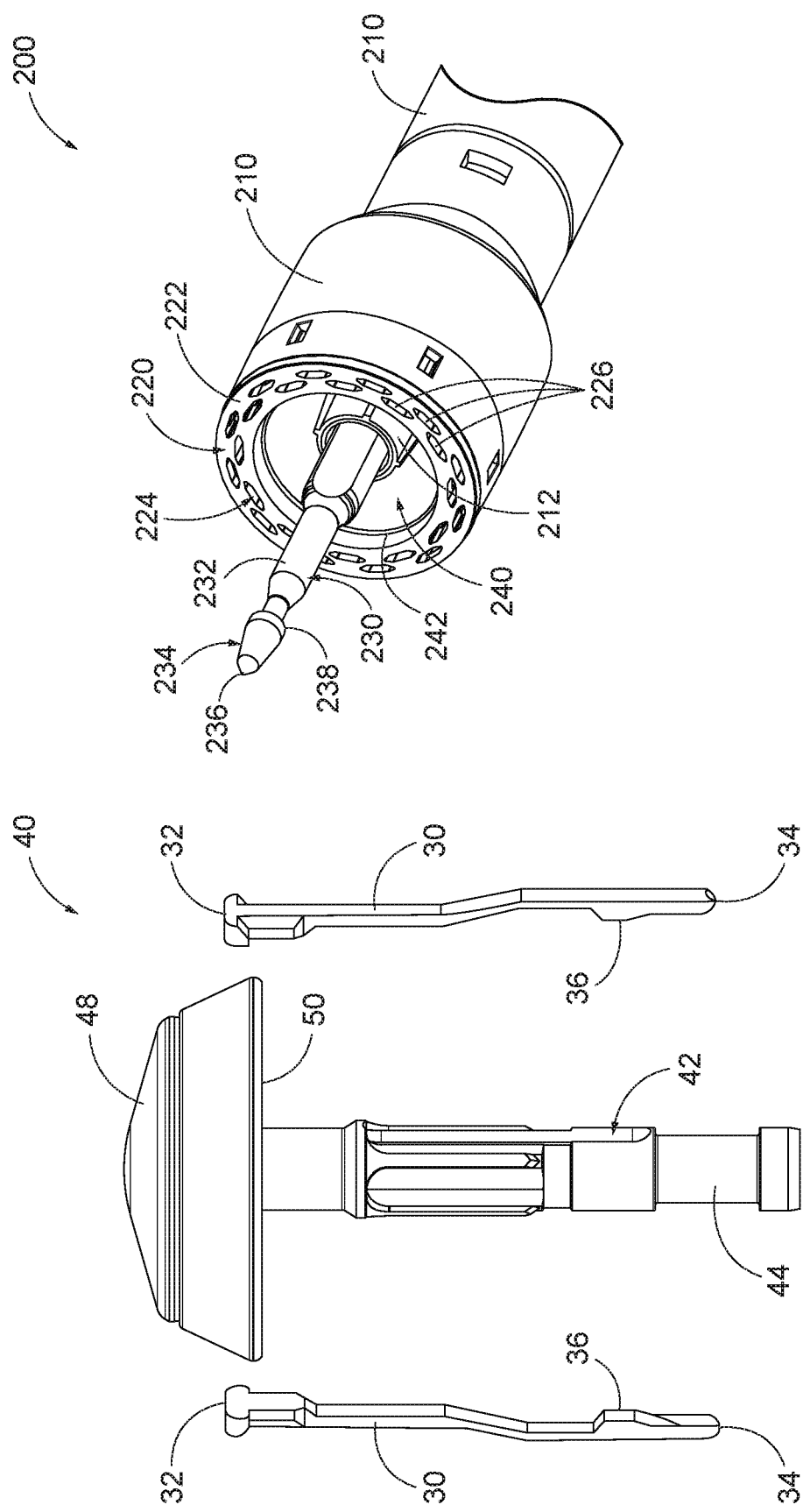

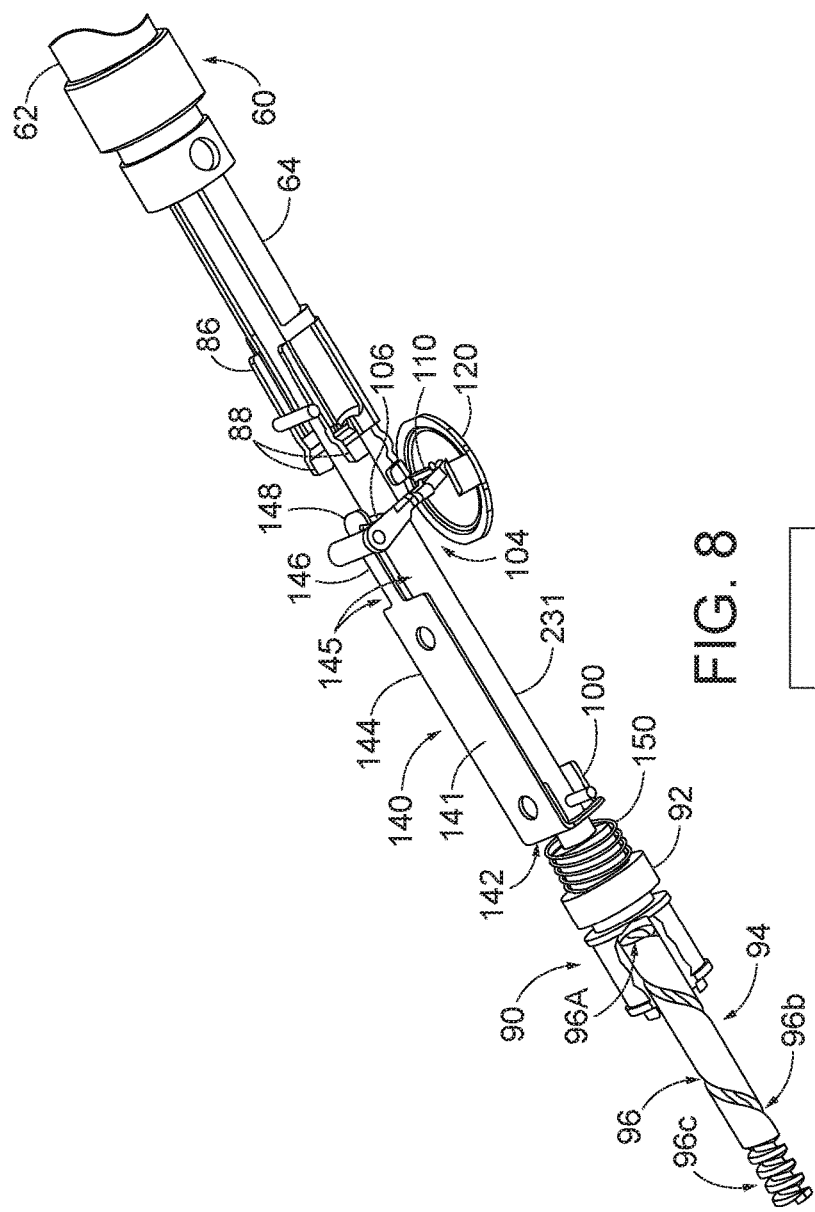
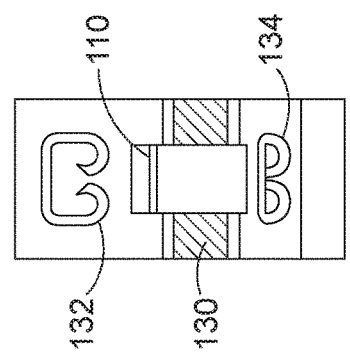

CIRCULAR STAPLING INSTRUMENT WITH FIRING TRIGGER HAVING INTEGRAL RESILIENT FEATURES

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4 depicts an exploded side elevational view of the anvil of FIG. 2;

FIG. 5 depicts a perspective view of a stapling head assembly of the surgical instrument of FIG. 1;

FIG. 8 depicts an enlarged partial perspective view of an exemplary indicator assembly of the surgical instrument of FIG. 1, showing an indicator window and indicator lever;

FIG. 9 depicts a diagrammatic view of the indicator window of FIG. 8, showing an exemplary indicator bar and exemplary corresponding staple representations;

Figure 1:
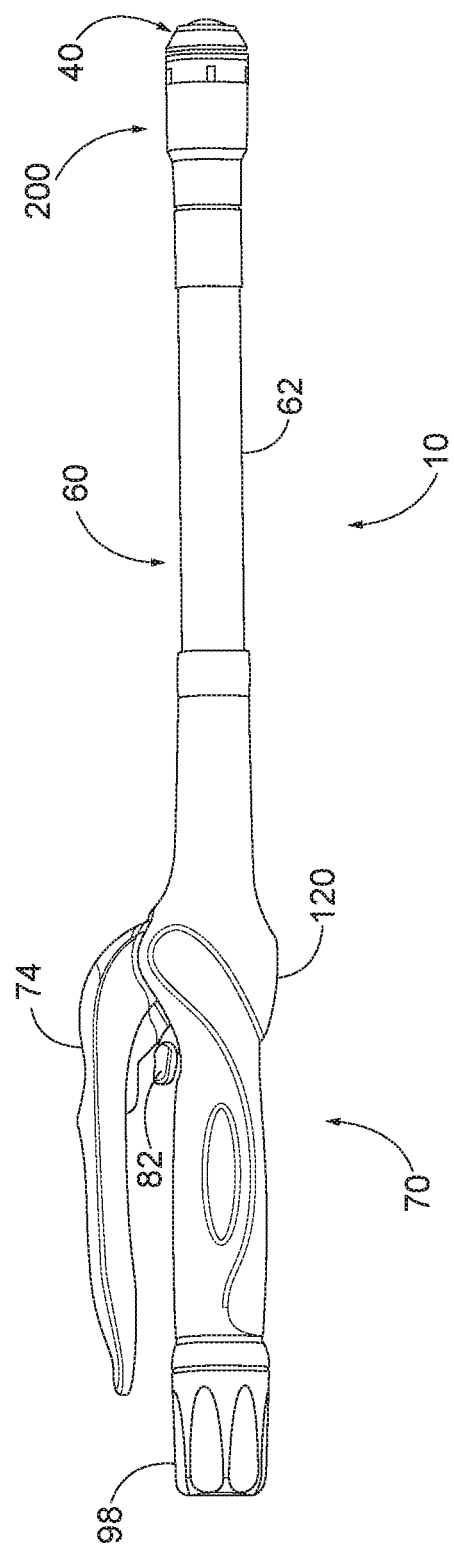
FIG. 1 depicts a side elevation view of an exemplary circular stapling surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-11 depict an exemplary circular surgical stapling instrument (10) having a stapling head assembly (200), a shaft assembly (60), and an actuator handle assembly (70), each of which will be described in more detail below. Shaft assembly (60) extends distally from actuator handle assembly (70) and stapling head assembly (200) is coupled to a distal end of shaft assembly (60). In brief, actuator handle assembly (70) is operable to actuate a staple driver member (250) of stapling head assembly (200) to drive a plurality of staples (66) out of stapling head assembly (200). Staples (66) are bent to form completed staples by an anvil (40) that is selectively attached at the distal end of instrument (10). Accordingly, tissue (2), as shown in FIGS. 10A-10E, may be stapled utilizing instrument (10).

In the present example, instrument (10) comprises a closure system and a firing system. As will be described in greater detail below, the closure system and anvil (40) are operable to clamp tissue between anvil (40) and stapling head assembly (200). As will also be described in greater detail below, the firing system and anvil (40) are operable to cut and staple tissue clamped between anvil (40) and stapling head assembly (200).

The closure system comprises a trocar (230), a trocar actuator (231), and an adjustment knob (98). Anvil (40) may be coupled to a distal end of trocar (230). Adjustment knob (98) is operable to longitudinally translate trocar (230) relative to stapling head assembly (200), thereby translating anvil (40) when anvil (40) is suitably coupled to trocar (230), and further clamping tissue between anvil (40) and stapling head assembly (200) as will be described in greater detail below.

The firing system comprises a trigger (74), a trigger actuation assembly (84), a driver actuator (64), and a staple driver member (250). Staple driver member (250) includes a knife member (240) configured to sever tissue when staple driver member (250) is actuated longitudinally. In addition, staples (66) are positioned distal to a plurality of staple drivers of staple driver member (250) such that staple driver member (250) also drives staples (66) distally when staple driver member (250) is actuated longitudinally. Thus, when trigger (74) is actuated and trigger actuation assembly (84) actuates staple driver member (250) via driver actuator (64), knife member (240) and staple drivers (252) substantially simultaneously sever tissue (2) and drive staples (66) distally relative to stapling head assembly (200) into tissue. The components and functionalities of the closure system and firing system will now be described in greater detail.

A. Exemplary Anvil

In the following discussion of anvil (40), the terms "distal" and "proximal" (and variations thereof) will be used with reference to the orientation of anvil (40) when anvil (40) is coupled with shaft assembly (60) of instrument (10). Thus, proximal features of anvil (40) will be closer to the operator of instrument (10); while distal features of anvil (40) will be further from the operator of instrument (10).

Figure 3:
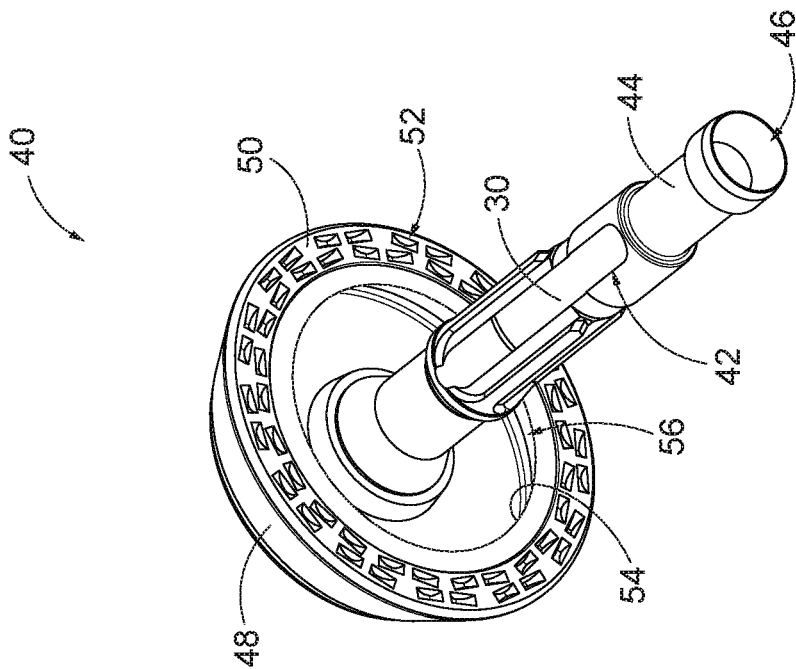
FIG. 3 depicts another perspective view of the anvil of FIG. 2.
Figure 2:
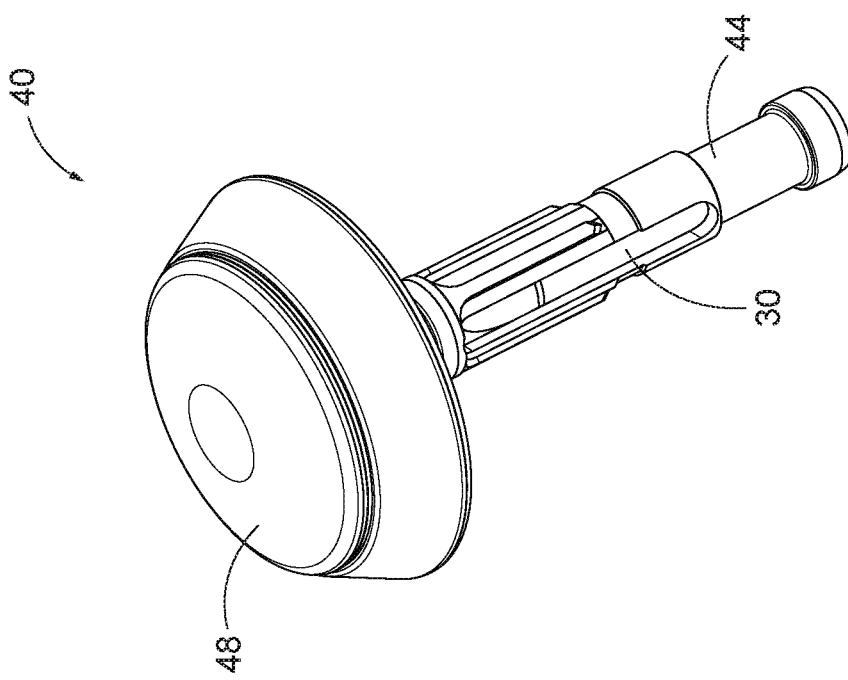
FIG. 2 depicts a perspective view of an exemplary anvil of the surgical instrument of FIG. 1.

As best seen in FIGS. 2-4, anvil (40) of the present example comprises a head (48) and a proximal shaft (44). As mentioned above and as will be described in greater detail below, anvil (40) of the present example may selectively couple to trocar (230) such that when coupled, movement of trocar (230) relative to stapling head assembly (200) also moves anvil (40) relative to stapling head assembly (200).

Head (48) includes a proximal surface (50) that defines a plurality of staple forming pockets (52). Staple forming pockets (52) are arranged in two concentric annular arrays. In some other versions, staple forming pockets (52) are arranged in three or more concentric annular arrays. Staple forming pockets (52) are configured to deform staples as the staples are driven into staple forming pockets (52). Accordingly, when anvil (40) is in the closed position and staples (66) are driven out of stapling head assembly (200) into staple forming pockets (52), each staple forming pocket (52) may deform a generally "U" shaped staple (66) into a "B" shape as is known in the art. As best seen in FIG. 3, proximal surface (50) terminates at an inner edge (54), which defines an outer boundary of an annular recess (56) surrounding proximal shaft (44).

Proximal shaft (44) defines a bore (46) and includes a pair of pivoting latch members (30) positioned in bore (46). As best seen in FIG. 4, each latch member (30) includes a "T" shaped distal end (32), a rounded proximal end (34), and a latch shelf (36) located distal to proximal end (34). "T" shaped distal ends (32) secure latch members (30) within bore (46). Latch members (30) are positioned within bore (46) such that distal ends (34) are positioned at the proximal ends of lateral openings (42), which are formed through the sidewall of proximal shaft (44). Lateral openings (42) thus provide clearance for distal ends (34) and latch shelves (36) to deflect radially outwardly from the longitudinal axis defined by proximal shaft (44). However, latch members (30) are configured to resiliently bias distal ends (34) and latch shelves (36) radially inwardly toward the longitudinal axis defined by proximal shaft (44). Latch members (30) thus act as retaining clips to allow anvil (40) to be selectively secured to trocar (230) of stapling head assembly (200). It should be understood, however, that latch members (30) are merely optional. Anvil (40) may be removably secured to a trocar (230) using any other suitable components, features, or techniques.

In addition to or in lieu of the foregoing, anvil (40) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; 8,910,847; U.S. Pub. No. 2016/0374671, issued as U.S. Pat. No. 10,188,389 on Jan. 29, 2019; and/or U.S. Pub. No. 2016/0374684, issued as U.S. Pat. No. 10,226,253 on Mar. 12, 2019, the disclosures of which are incorporated by reference herein. Still other suitable configurations will be apparent to one of ordinary skill in the art in view of the teachings herein.

B. Exemplary Stapling Head Assembly

Figure 6:
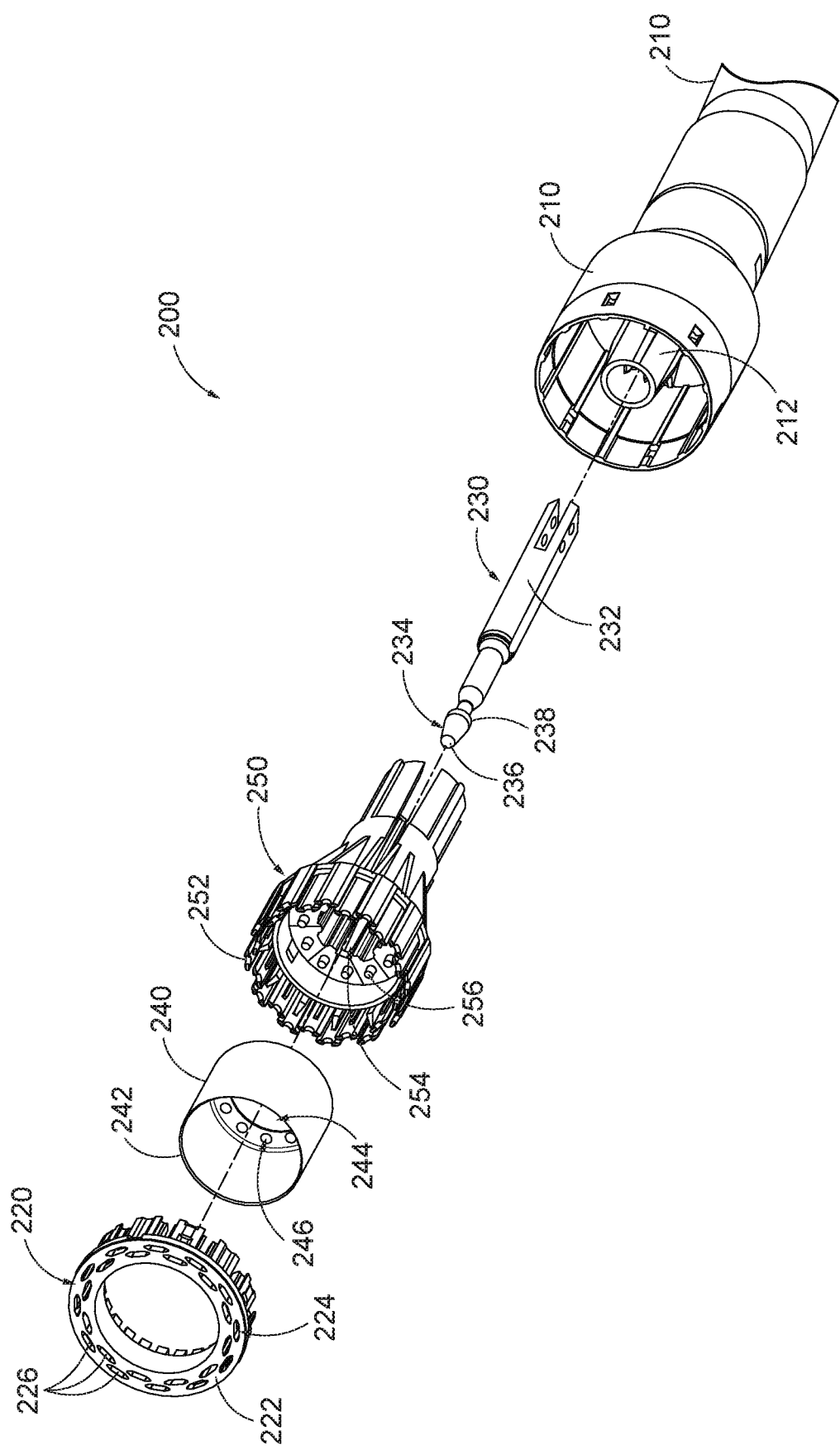
FIG. 6 depicts an exploded perspective view of the stapling head assembly of FIG. 5.

As best seen in FIGS. 5-6, stapling head assembly (200) of the present example is coupled to a distal end of shaft assembly (60) and comprises a tubular casing (210) housing a slidable staple driver member (250). A cylindraceous inner core member extends distally within tubular casing (210). Tubular casing (210) is fixedly secured to an outer sheath (62) of shaft assembly (60), such that tubular casing (210) serves as a mechanical ground for stapling head assembly (200).

Trocar (230) is positioned coaxially within inner core member (212) of tubular casing (210). As mentioned above and as will be described in greater detail below, trocar (230) is operable to translate distally and proximally relative to tubular casing (210) in response to rotation of adjustment knob (98) relative to casing (110) of handle assembly (100). Trocar (230) comprises a shaft (232) and a head (234). Head (234) includes a pointed tip (236) and an inwardly extending proximal surface (238). Shaft (232) thus provides a reduced outer diameter just proximal to head (234), with surface (238) providing a transition between that reduced outer diameter of shaft (232) and the outer diameter of head (234). While tip (236) is pointed in the present example, tip (236) is not sharp. Tip (236) will thus not easily cause trauma to tissue due to inadvertent contact with tissue. Head (234) and the distal portion of shaft (232) are configured for insertion in bore (46) of anvil (40). Proximal surface (238) and latch shelves (36) have complementary positions and configurations such that latch shelves (36) engage proximal surface (238) when proximal shaft (44) of anvil (40) is fully seated on trocar (230). Anvil (40) may thus secure to trocar (230) through a snap fitting between latch members (30) and head (234). In addition, or in the alternative, trocar (230) may include a magnetic portion (not shown) which may attract anvil (40) towards trocar (230). Still further configurations and arrangements for anvil (40) and trocar (230) will be apparent to one of ordinary skill in the art in view of the teachings herein.

Figure 10A:
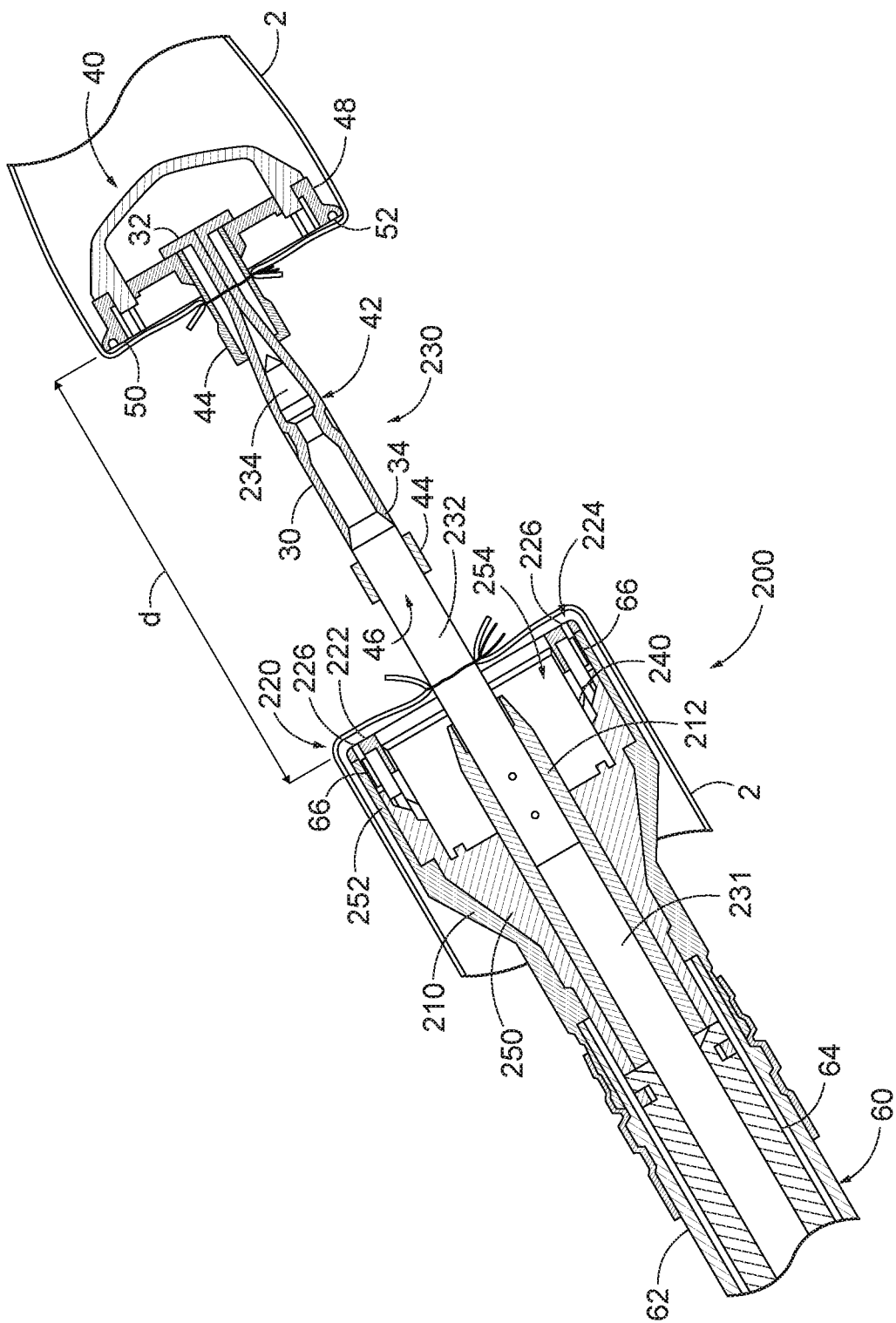
FIG. 10A depicts an enlarged longitudinal cross-section view of the stapling head assembly of FIG. 5, showing the anvil of FIG. 2 in a first open position, where the anvil is within a first tubular portion of tissue and the stapling head assembly is within a second tubular portion of tissue.
Figure 10B:
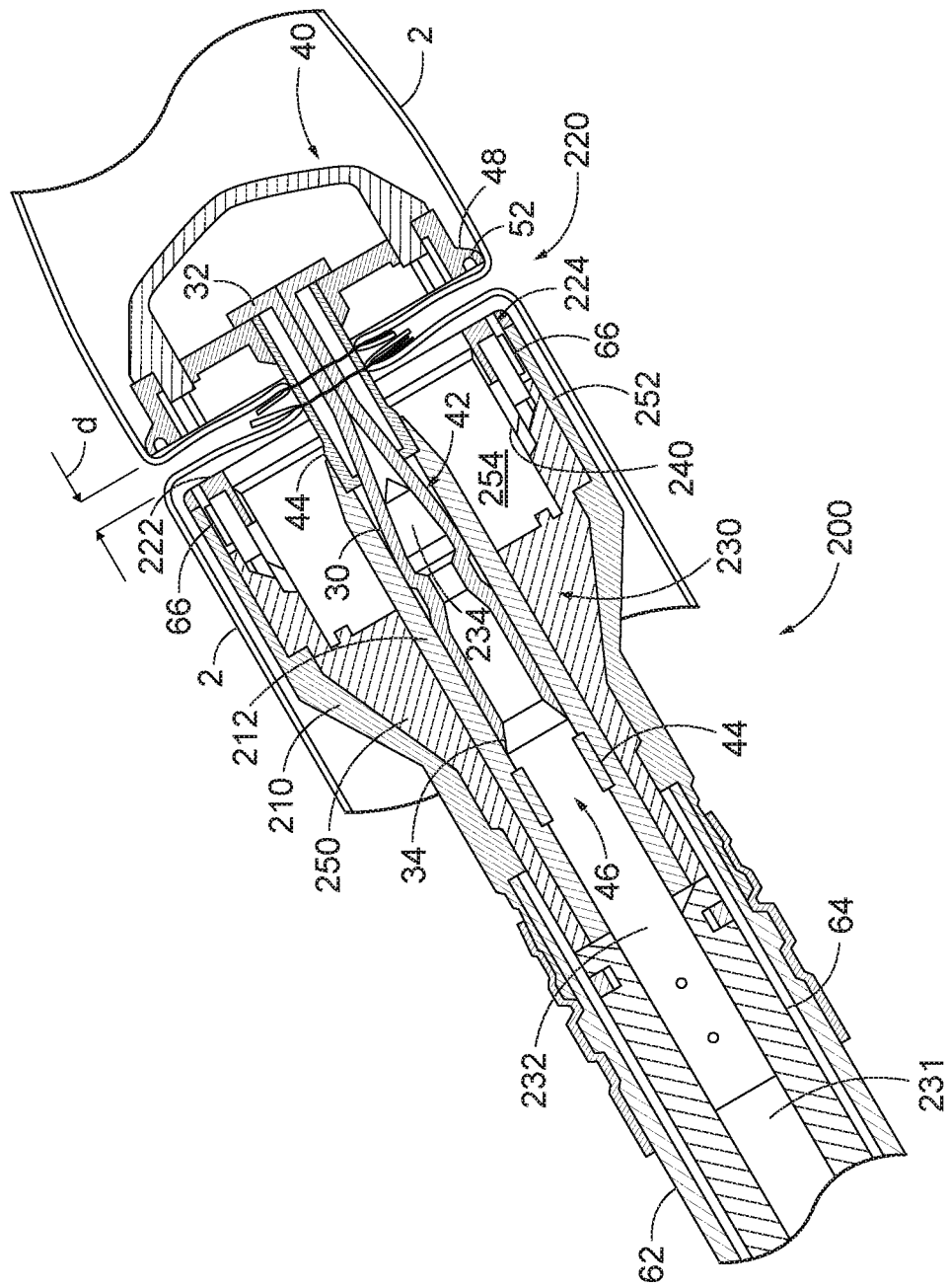
FIG. 10B depicts an enlarged longitudinal cross-sectional view of the stapling head assembly of FIG. 5, showing the anvil of FIG. 2 in a closed position, where the anvil is within the first tubular portion of tissue and the stapling head assembly is within the second tubular portion of tissue.

Staple driver member (250) is operable to actuate longitudinally within tubular casing (210) in response to rotation of trigger (74) of actuator handle assembly (70) as will be described in greater detail below. Staple driver member (250) includes two distally presented concentric annular arrays of staple drivers (252). Staple drivers (252) are arranged to correspond with the arrangement of staple forming pockets (52) described above. As best seen in FIGS. 10A-10B, each staple driver (252) is located underneath a corresponding staple (66). The arrangement of staple drivers (252) may be modified just like the arrangement of staple forming pockets (52) as described above. Staple driver member (250) also defines a bore (254) that is configured to coaxially receive core member (212) of tubular casing (210). An annular array of studs (256) project distally from a distally presented surface surrounding bore (254).

A cylindraceous knife member (240) is coaxially positioned within staple driver member (250). Knife member (240) includes a distally presented, sharp circular cutting edge (242). Knife member (240) is sized such that knife member (240) defines an outer diameter that is smaller than the diameter defined by the inner annular array of staple drivers (252). Knife member (240) also defines an opening that is configured to coaxially receive core member (212) of tubular casing (210). An annular array of openings (246) formed in knife member (240) is configured to complement the annular array of studs (256) of staple driver member (250), such that knife member (240) is fixedly secured to staple driver member (250) via studs (256) and openings (346). Therefore, when stapling driver member (250) is actuated relative to tubular casing (210), so is knife member (240). Other suitable structural relationships between knife member (240) and stapler driver member (250) will be apparent to those of ordinary skill in the art in view of the teachings herein.

A deck member (220) is fixedly secured to tubular casing (210). Deck member (220) includes a distally presented deck surface (222) defining two concentric annular arrays of staple openings (224), where each staple opening (224) has its own staple pocket (226) housing a staple (66). Staple openings (224) and staple pockets (226) are arranged to correspond with the arrangement of staple drivers (252) and staple forming pockets (52) described above. Accordingly, when staple driver member (250) is actuated distally relative to tubular casing (210) in response to rotation of trigger (74), each staple driver (252) drives a corresponding staple (66) out of its staple pocket (226) and through a corresponding staple opening (224) of deck member (220). When anvil (40) is in the closed position, staples (66) are driven into a corresponding staple forming pockets (52) to bend legs (68) of the staples (66), thereby stapling the material located between anvil (40) and stapling head assembly (200).

The arrangement of staple openings (224) may be modified just like the arrangement of staple forming pockets (52) as described above. It should also be understood that various structures and techniques may be used to contain staples (66) within stapling head assembly (200) before stapling head assembly (200) is actuated. Such structures and techniques that are used to contain staples within stapling head assembly (200) may prevent the staples from inadvertently falling out through staple openings (224) before stapling head assembly (200) is actuated. Various suitable forms that such structures and techniques may take will be apparent to those of ordinary skill in the art in view of the teachings herein.

As best seen in FIG. 6, deck member (220) defines an inner diameter that is just slightly larger than the outer diameter defined by knife member (240). Deck member (220) is thus configured to allow knife member (240) to translate distally to a point where cutting edge (242) is distal to deck surface (222).

In addition to or in lieu of the foregoing, stapling head assembly (200) may be further constructed and operable in accordance with at least some of the teachings of U.S. 5,205,459; 5,271,544; 5,275,322; 5,285,945; 5,292,053;

5,333,773; 5,350,104; 5,533,661; 8,910,847; U.S. Pub. No. 2016/0374671, issued as U.S. Pat. No. 10,188,386 on Jan. 29, 2019; and/or U.S. Pub. No. 2016/0374684, issued as U.S. Pat. No. 10,226,253 on Mar. 12, 2019, the disclosures of which are incorporated by reference herein. Still other suitable configurations will be apparent to one of ordinary skill in the art in view of the teachings herein.

C. Exemplary Shaft Assembly

Figure 7A:
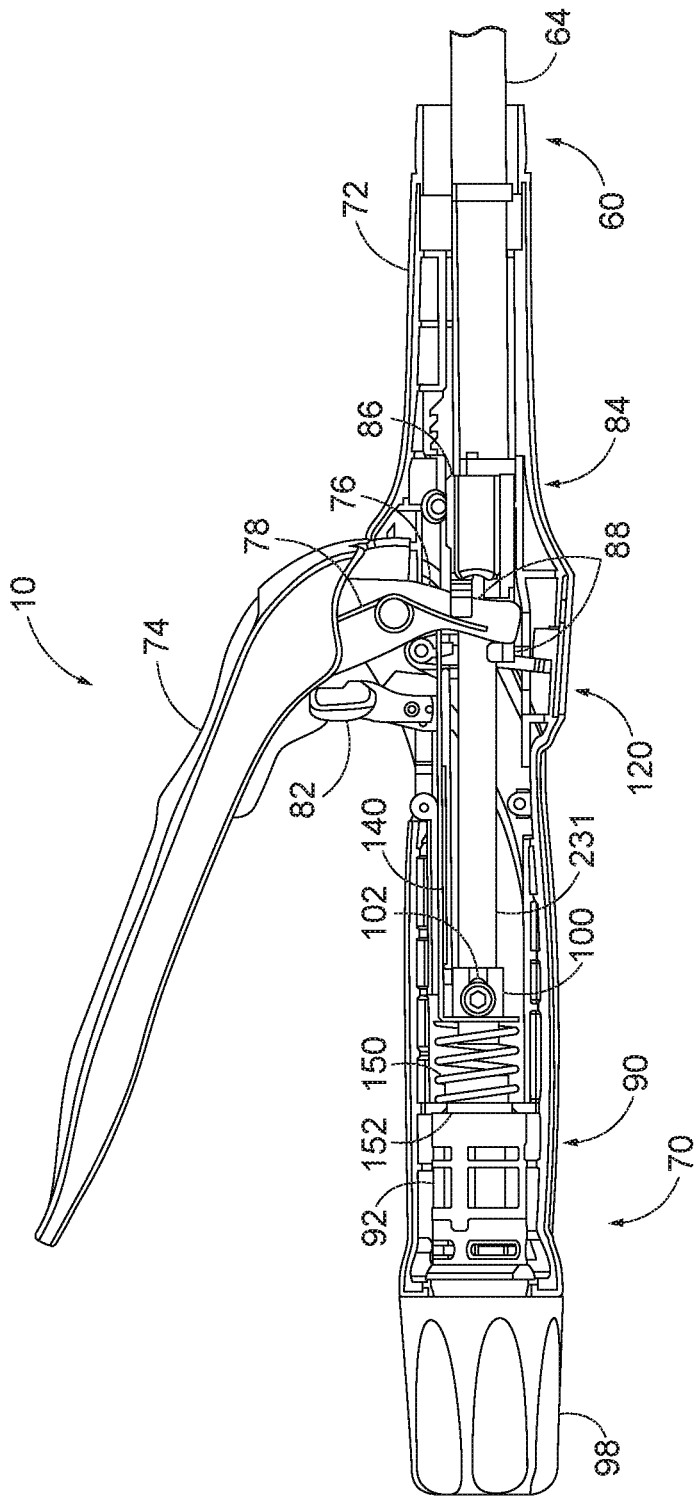
FIG. 7A depicts an enlarged side elevation view of an exemplary actuator handle assembly of the surgical instrument of FIG. 1 with a portion of the body removed, showing a trigger in an unfired position and a lockout feature in a locked position.
Figure 7B:
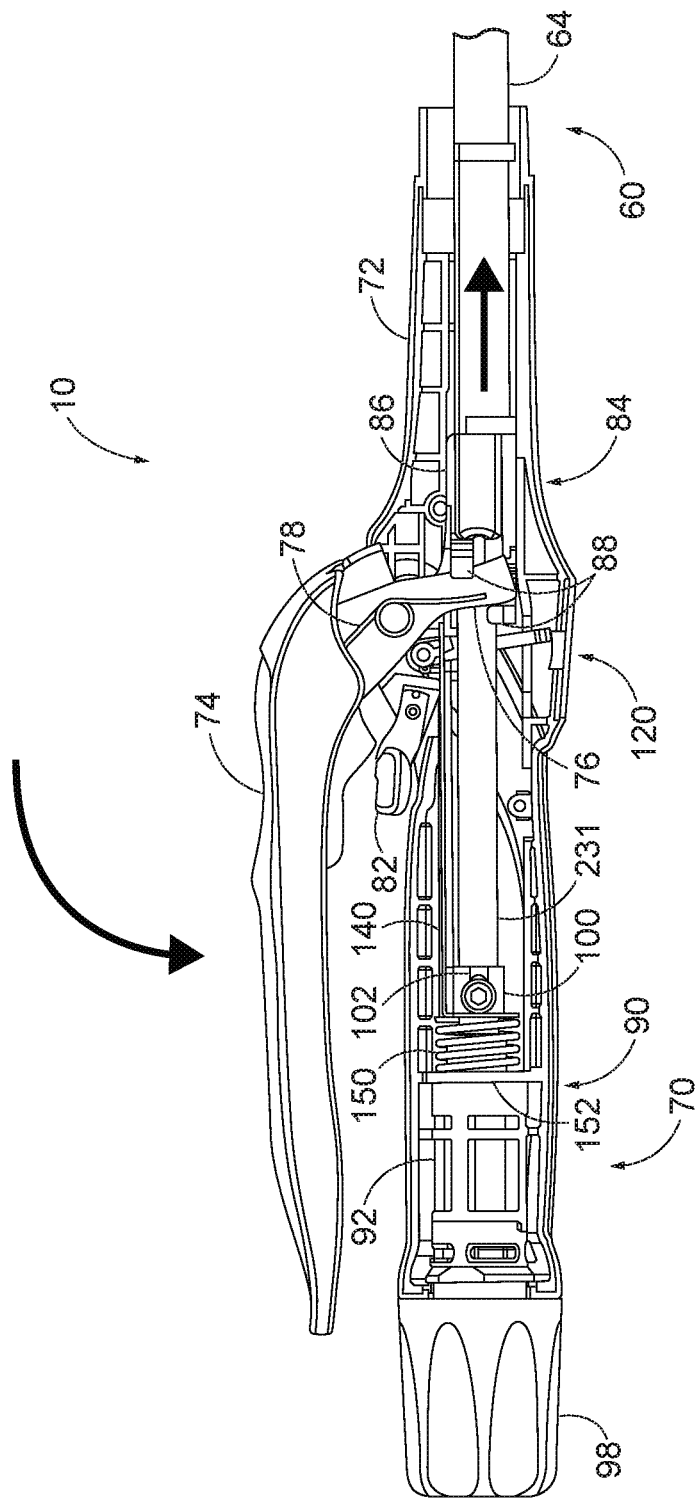
FIG. 7B depicts an enlarged side elevation view of the actuator handle assembly of FIG. 7A, showing the trigger in a fired position and the lockout feature in an unlocked position.

Stapling head assembly (200) and trocar (230) are positioned at a distal end of shaft assembly (60), as shown in FIGS. 10A-10D. Shaft assembly (60) of the present example comprises an outer tubular member (62) and a driver actuator (64). Outer tubular member (62) is coupled to tubular casing (210) of stapling head assembly (200) and to a body (72) of actuator handle assembly (70), thereby providing a mechanical ground for the actuating components therein. As seen in FIGS. 7A-7B, the proximal end of driver actuator (64) is coupled to a trigger actuation assembly (84) of actuator handle assembly (70), as described below. The distal end of driver actuator (64) is coupled to staple driver member (250) such that the rotation of trigger (74) longitudinally actuates staple driver member (250). As shown in FIGS. 10A-10D, driver actuator (64) comprises a tubular member having an open longitudinal axis such that trocar actuator (231), which is coupled to trocar (230), may actuate longitudinally within and relative to driver actuator (64). Other components may be disposed within driver actuator (64) as will be apparent to one of ordinary skill in the art in view of the teachings herein.

In the present example, shaft assembly (60) is substantially straight. However, shaft assembly (60) may extend distally from actuator handle assembly (70) with a preformed bend. In some versions, the preformed bend is configured to facilitate positioning of stapling head assembly (200) within a patient's colon. Various suitable bend angles or radii that may be used will be apparent to those of ordinary skill in the art in view of the teachings herein. In examples where shaft assembly (60) includes a preformed bend, actuator (231) may be coupled with trocar (230) via a flexible band portion (not shown). Flexible band portion (not shown) may extend from a distal end of actuator (231), located proximal to the preformed bend, to couple with trocar (230), located distal to the preformed bend. Flexible band portion (not shown) may be dimensioned to flex during translation along the longitudinal profile of the preformed bend of shaft assembly (60). In such cases, trocar actuator (231) may be slidably housed within actuator handle assembly (70), while trocar (230) is slidably housed within tubular casing (210). Flexible band portion (not shown) may be connected to both trocar (230) and actuator (231) via pins.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661; U.S. Pub. No. 2012/0292372, issued as U.S. Pat. No. 8,910,847 on Dec. 16, 2014; and/or U.S. Pub. No. 2015/0083773 as U.S. Pat. No. 9,936,949 on Apr. 10, 2018, the disclosures of which are incorporated by reference herein; and/or in accordance with other configurations as will be apparent to one of ordinary skill in the art in view of the teachings herein.

D. Exemplary Actuator Handle Assembly

Referring now to FIGS. 7A-8, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 7A) to a fired position (shown in FIG. 7B) actuates driver actuator (64) described above. A spring (78) is coupled to body (72) and trigger (74) to bias trigger (74) towards the unfired position. Lockout feature (82) is a pivotable member that is coupled to body (72). In a first, locked position, as shown in FIG. 7A, lockout feature (82) is pivoted upwards and away from body (72) such that lockout feature (82) engages trigger (74) and mechanically resists actuation of trigger (74) by a user. In a second, unlocked position, such as that shown in FIGS. 1 and 7B, lockout feature (82) is pivoted downward such that trigger (74) may be actuated by the user. Accordingly, with lockout feature (82) in the second position, trigger (74) can engage a trigger actuation assembly (84) to fire instrument F.

As shown in FIGS. 7A-7B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661; U.S. Pub. No. 2012/0292372, issued as U.S. Pat. No. 8,910,847 on Dec. 16, 2014; and/or U.S. Pub. No. 2015/0083773 , issued as U.S. Pat. No. 9,936,949 on Apr. 10, 2018, the disclosures of which are incorporated by reference herein; and/or in accordance with other configurations as will be apparent to one of ordinary skill in the art in view of the teachings herein.

Body (72) also houses trocar actuation assembly (90) configured to actuate trocar (230) longitudinally in response to rotation of adjustment knob (98). As best shown in FIGS. 7A-8, trocar actuation assembly (90) of the present example comprises adjustment knob (98), a grooved shank (94), and a sleeve (92). Grooved shank (94) of the present example is located at a proximal end of trocar actuator (231). In other versions, grooved shank (94) and trocar actuator (231) may alternatively be separate components that engage to transmit longitudinal movement. While grooved shank (94) is configured to translate within body (72), grooved shank (94) does not rotate within body (72). Adjustment knob (98) is rotatably supported by the proximal end of body (72) and is operable to rotate sleeve (92), which is engaged with grooved shank (94) via an internal tab (not shown). Adjustment knob (98) also defines internal threading (not shown) as will be described in greater detail below. Grooved shank (94) of the present example comprises a continuous groove (96) formed in the outer surface of grooved shank (94). Accordingly, when adjustment knob (98) is rotated, the internal tab of sleeve (92) rides within groove (96) and grooved shank (94) is longitudinally actuated relative to sleeve (92). Since grooved shank (94) is located at the proximal end of trocar actuator (231), rotating adjustment knob (98) in a first direction advances trocar actuator (231) distally relative to actuator handle assembly (70). When trocar (230) is coupled with anvil (40), anvil (40) also advances distally relative to stapling head assembly (200)

thereby increasing the distance between proximal surface (50) of the anvil (40) and distally presented deck surface (222) of deck member (220), otherwise known as a gap distance d. By rotating adjustment knob (98) in the opposite direction, trocar actuator (231) is actuated proximally relative to actuator handle assembly (70) to reduce the gap distance d between anvil (40) and stapling head assembly (200) when trocar (230) is coupled with anvil (40). Thus, trocar actuation assembly (90) is operable to actuate trocar (230) in response to rotating adjustment knob (98). Other suitable configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial length of grooved shank (94). Middle portion (96B) comprises a section with comparably coarser pitch or fewer grooves per axial length such that relatively few rotations are required for the internal tab of sleeve (92) to traverse along axial distance. When anvil (40) is in an initial, distal position in relation to stapling head assembly (200) (as shown in FIG. 10A) the internal tab of sleeve (92) is positioned in middle portion (96B). Accordingly, the gap distance d may be quickly reduced through relatively few rotations of adjustment knob (98) while the internal tab of sleeve (92) traverses middle portion (96B). Proximal portion (96C) of the present example is substantially like distal portion (96A) and comprises a fine pitch or a high number of grooves over a short axial distance of grooved shank (94) such that many rotations are required to traverse the short axial distance. Proximal portion (96C) of the present example is engaged by the internal threading defined by knob (98) when anvil (40) is substantially near to stapling head assembly (200) (as shown in FIG. 10B), such that indicator bar (110) moves within indicator window (120) along scale (130) to indicate that the anvil gap is within a desired operating range, as will be described in more detail below. Accordingly, when grooved shank (94) reaches a proximal position where the proximal portion (96C) of groove (96) engages the internal threading of knob (98), each rotation of adjustment knob (98) may reduce the gap distance d by a relatively small amount to provide for fine tuning. The internal tab of sleeve (92) may be disengaged from groove (96) when proximal portion (96C) is engaged with the internal threading of knob (98).

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2015/0083773, issued as U.S. Pat. No. 9,936,949 on Apr. 10, 2018, the disclosures of which are incorporated by reference herein; and/or in accordance with other configurations as will be apparent to one of ordinary skill in the art in view of the teachings herein.

As noted above, gap distance d corresponds to the distance between anvil (40) and stapling head assembly (200). When instrument (10) is inserted into a patient, this gap distance d may not be easily viewable. Accordingly, a moveable indicator bar (110), shown in FIGS. 8-9, is provided to be visible through an indicator window (120) positioned opposite to trigger (74). As will be described in greater detail below, indicator bar (110) is operable to move in response to rotation of adjustment knob (98) such that the position of indicator bar (110) is representative of the gap distanced. As shown in FIG. 9, indicator window (120) further comprises a scale (130) which indicates that the anvil gap is within a desired operating range (e.g., a green colored region or "green zone") and a corresponding staple compression representation at each end of scale (130). By way of example only, as shown in FIG. 9, a first staple image (132) depicts a large staple height while a second staple image (134) depicts a small staple height. Accordingly, a user can view the position of the coupled anvil (40) relative to the stapling head assembly (200) via indicator bar (110) and scale (130). The user may then adjust the positioning of anvil (40) via adjustment knob (98) accordingly.

In the example shown in FIGS. 7A-8, a U-shaped clip (100) is attached to an intermediate portion of trocar actuator (231) located distally of grooved shank (94). In the present example, an extension of trocar actuator (231) engages a slot in the housing of handle assembly (70) to prevent trocar actuator (231) from rotating about its axis when adjustment knob (98) is rotated.

Because trocar actuator (231) and trocar (230) are two separate components joined together during assembly, a tolerance stack may occur once trocar (230) and trocar actuator (231) are assembled and suitably incorporated into instrument (10). To accommodate for this potential tolerance stack, it may be necessary to calibrate the proper placement of trocar actuator (231) within instrument (10) such that indicator bar (110) may show a proper gap distance d during exemplary use. U-shaped clip (100) of the present example further includes an elongated slot (102) on each of its opposite sides for receiving an attachment member, such as a screw, bolt, pin, etc., to selectively adjust the longitudinal position of elongated slot (102) of U-shaped clip (100) relative to trocar actuator (231) for purposes of calibrating indicator bar (110) relative to scale (130). In some versions, the attachment member (e.g., screw, bolt, pin, etc.) engages with a portion of body (72) to substantially prevent trocar actuator (231) from rotating about its axis when adjustment knob (98) is rotated.

As shown in FIG. 8, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (231) and/or grooved shank (94). A coil spring (150) is interposed between flange (142) and a boss (152) to bias flange (142) against U-shaped clip (100). Accordingly, when U-shaped clip (100) actuates distally with trocar actuator (231) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (231) and/or grooved shank (94) translate proximally, thereby compressing coil spring (150). In some versions, indicator bracket (140) may be fixedly attached to trocar actuator (231) and/or grooved shank (94).

In the present example, a portion of lockout feature (82) abuts a surface (141) of indicator bracket (140) when indicator bracket (140) is in a longitudinal position that does not correspond to when gap distance d is within a desired operating range (e.g., a green colored region or "green zone"). When gap distance d is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between proximal surface (50) of anvil (40) and distally presented deck surface (222) of deck member (220).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, issued as U.S. Pat. No. 8,910,847 on Dec. 16, 2014; and/or U.S. Pub. No. 2015/0083773, issued as U.S. Pat. No. 9,936,949 on Apr. 10, 2018, the disclosures of which are incorporated by reference herein; and/or in accordance with other configurations as will be apparent to one of ordinary skill in the art in view of the teachings herein.

E. Exemplary Use of Circular Stapling Surgical Instrument

FIGS. 7A-7B and FIGS. 10A-10E show an exemplary use of circular stapling surgical instrument (10) in accordance with the description above. As mentioned above, anvil (40) may selectively couple with trocar (230) such that movement of trocar (230) relative to tubular casing (210) and deck member (220) leads to movement of anvil (40) relative to tubular casing (210) and deck member (220). With anvil (40) as a separate component, it should be understood that anvil (40) may initially be inserted and secured to a portion of tissue (2) prior to being coupled with trocar (230). By way of example only, anvil (40) may be inserted into and secured to a first tubular portion of tissue (2) while stapling head assembly (200) is inserted into and secured to a second tubular portion of tissue (2). For instance, the first tubular portion of tissue (2) may be sutured to or about a portion of anvil (40), and the second tubular portion of tissue (2) may be sutured to or about trocar (230).

As shown in FIG. 10A, anvil (40) may then be coupled to trocar (230) in accordance with the description above, such as a snap fitting between latch members (30) of anvil (40) and head (234) of trocar (230). In FIG. 10A, trocar (230) is shown in a distal most actuated position. Trocar (230) may be actuated to the distal most actuated position by rotation of knob (98) in accordance with the description above. Such an extended position for trocar (230) may provide a larger area to which tissue (2) may be coupled prior to attachment of anvil (40). The extended position of trocar (230) may also provide for easier attachment of anvil (40) to trocar (230). At the position shown in FIG. 10A, trigger (74) is locked in the position shown in FIG. 7A by lockout feature (82), as lockout feature (82) may not pivot to unlock trigger (74) due to interference caused by surface (141) of indicator bracket (140) in accordance with the description above.

As mentioned above, when anvil (40) is coupled to trocar (230), rotation of adjustment knob (98) may translate both trocar (230) and anvil (40), thereby enlarging or reducing gap distanced. For instance, as shown sequentially in FIGS. 10A-10B, anvil (40) is shown actuating proximally relative to actuator handle assembly (70) from an initial, open position (FIG. 10A) to a closed position (FIG. 10B) where gap distance d is brought within a suitable predetermined range. When gap distance d is brought within a suitable predetermined range, indicator bar (110) may move within indicator window (120) to show the relative gap distance d is within a desired operating range (e.g. a green colored region or "green zone") in accordance with the description above. Additionally, shown between FIGS. 7A-7B, when gap distance d is brought within a suitable predetermined range, lockout feature (82) may be pivoted relative to body (72) to an unlocked position and trigger (74) may pivot relative to body (72) to engage trigger actuation assembly (84) in accordance with the description above.

Figure 10C:
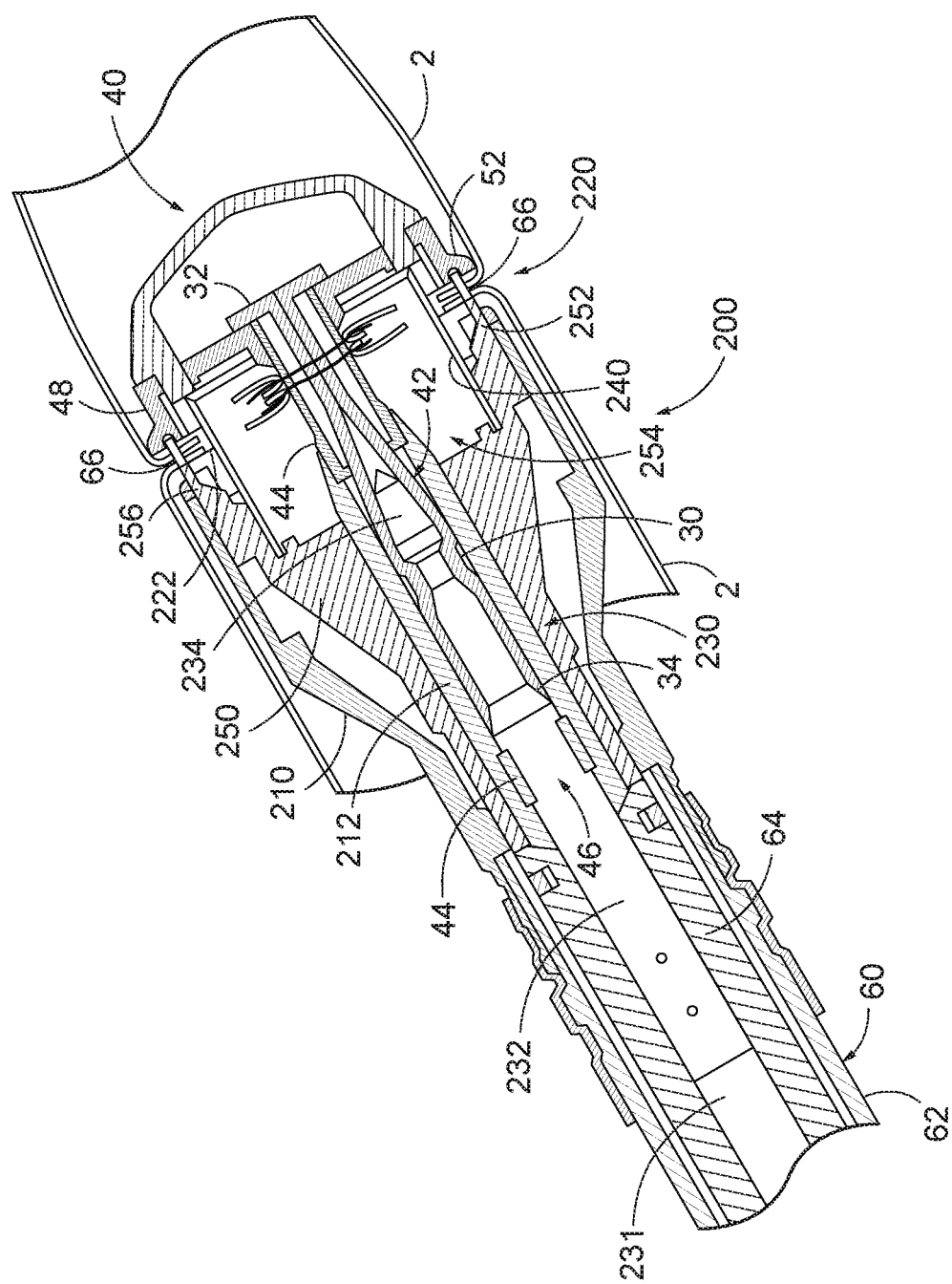
FIG. 10C depicts an enlarged longitudinal cross-sectional view of the stapling head assembly of FIG. 5, showing the anvil of FIG. 2 in the closed position, were an exemplary staple driver and blade are in a fired position such that the first tubular portion of tissue and the second tubular portion of tissue are stapled together with excess tissue severed.

As shown in FIG. 7B, with lockout feature (82) pivoted into the unlocked position, trigger (74) is pivoted toward body (72) such that trigger arms (76) drive against tabs (88) to distally actuate slidable trigger carriage (86) and driver actuator (64). As shown in FIG. 10C, distal actuation of driver actuator (64) drives slidable staple driver member (250), staples drivers (252), and cylindraceous knife member (240) distally. Distal advancement of staple drivers (252) drive staples (66) against corresponding staple forming pockets (52) thereby stapling tissue (2) between anvil (40) and stapling head assembly (200) to form a continuous tubular portion of tissue (2). Additionally, distal advancement of cylindraceous knife member (240) severs excess tissue located radially interior to newly formed staples (66). Stapling head assembly (200) is operable to staple and sever tissue (2) by a user pivoting a trigger (74) of actuator handle assembly (70), as will be described in greater detail below.

Figure 10D:
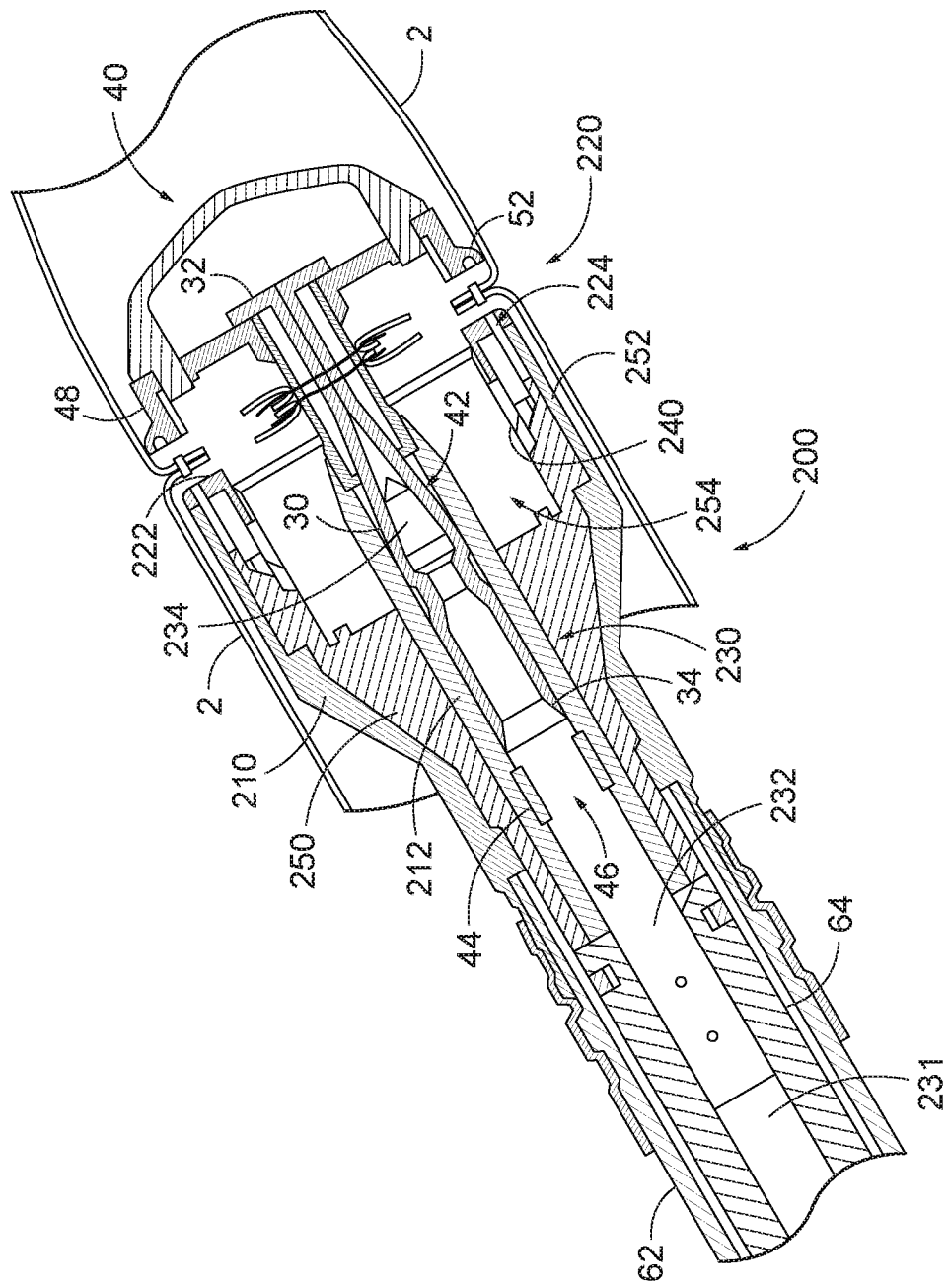
FIG. 10D depicts an enlarged longitudinal cross-sectional view of the stapling head assembly of FIG. 5, showing the anvil of FIG. 2 in a second open position, where the first tubular portion of tissue and the second tubular portion of tissue are attached.
Figure 10E:
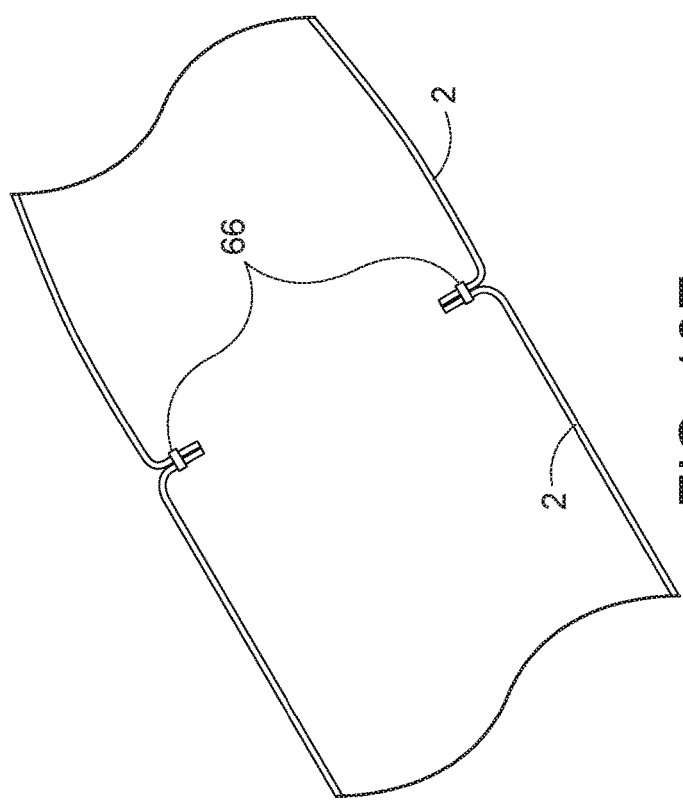
FIG. 10E depicts an enlarged longitudinal cross-section view of the first tubular portion and the second tubular portion after the stapling head assembly of FIG. 5 and the anvil of FIG. 2 have been removed, leaving a completed end-to-end anastomosis.
Figure 11:
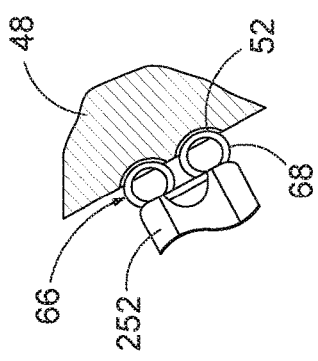
FIG. 11 depicts an enlarged partial cross-sectional view of an exemplary staple formed against the anvil of FIG. 2.

As best shown in FIG. 10D, once trigger (74) has been actuated to staple and sever tissue (2), a user may then turn rotatable knob (98) to distally advance anvil (40), thereby releasing portions of tissue (2) grasped between proximal surface (50) of anvil (40) and distally presented deck surface (222) of deck member (220). As best shown in FIG. 10E, with previously grasped tissue (2) released, a user may then remove instrument (10), thereby leaving a continuous tubular portion of tissue (2) behind.

II. Exemplary Alternative Circular Stapling Surgical Instrument

As described above, trigger (74) of instrument is pivotably mounted to body (72), while a separate spring (78) is coupled to both body (72) and trigger (74) in order to resiliently bias trigger (74) toward an unfired position. However, use of a separate spring (78) as a biasing mechanism between trigger (74) and body (72) may add to component and assembly costs and take up an unnecessary amount of space within the interior of body (72). Therefore, it may be desirable to provide for a trigger having an integral resilient feature that directly interacts with a body of an instrument to bias the trigger toward an open position.

A. Overview of Exemplary Circular Stapling Surgical Instrument

Figure 12:
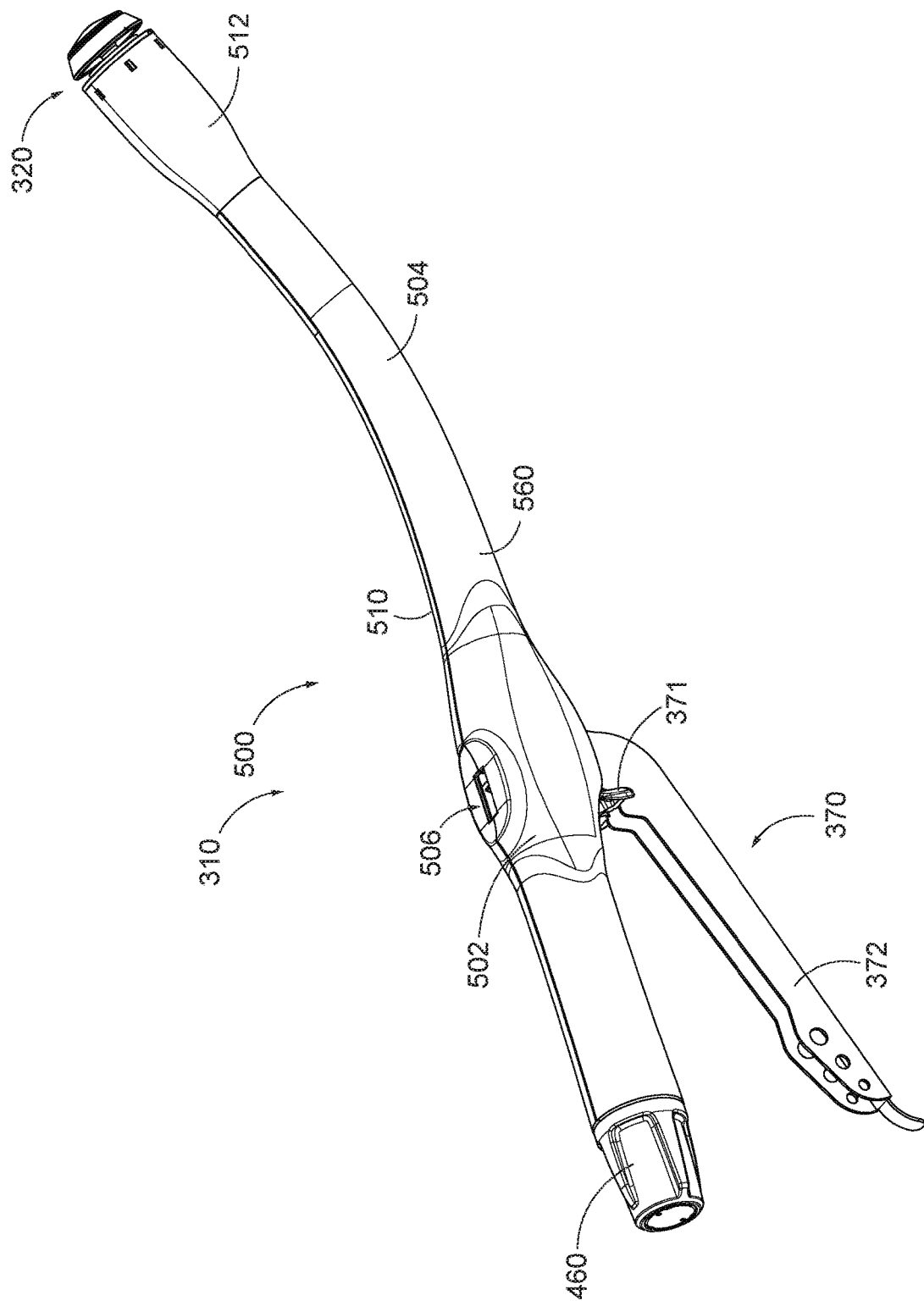
FIG. 12 depicts a perspective view of an exemplary alternative circular stapling surgical instrument.
Figure 13:
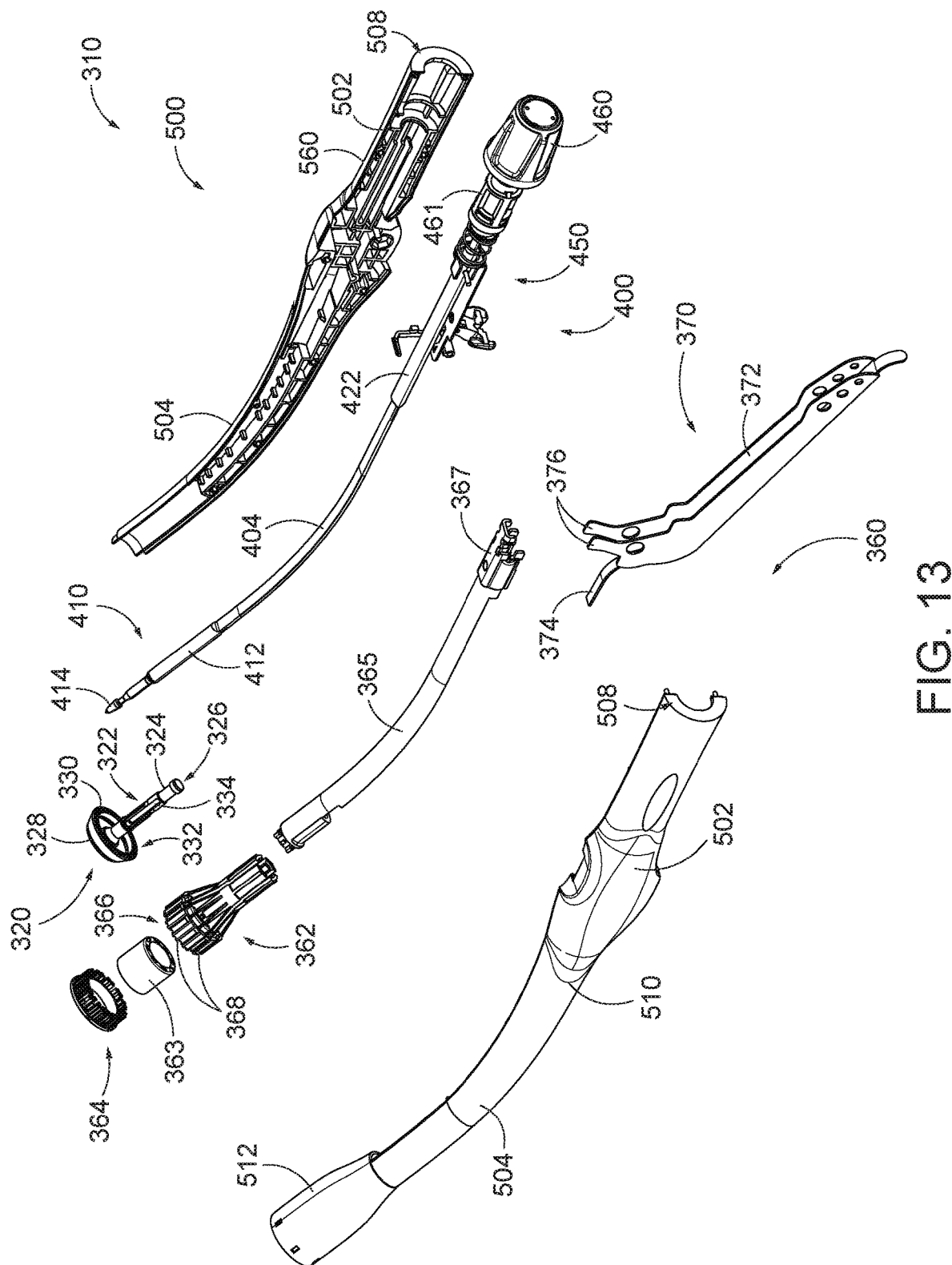
FIG. 13 depicts an exploded perspective view of the surgical instrument of FIG. 12.

FIGS. 12-13 show an exemplary circular stapling surgical instrument (310) that may be used in replacement of instrument (10) described above. Therefore, instrument (310) may perform substantially similarly as instrument (10) describe above, with differences described below. Instrument (310) includes an anvil (320), a firing system (360), a closure system (400), and a casing assembly (500). In brief, closure system (400) and anvil (320) are operable to clamp tissue between anvil (320) and a deck member (364) of firing system (360); while firing system (360) and anvil (40) are operable to cut and staple tissue clamped between anvil (320) and deck member (364). As will be described in greater detail below, firing system (360) includes a trigger (370) having a lever (372) with an integrated leaf spring (374). As will also be described in greater detail below, trigger (370) having an integrated leaf spring (374) configured to bias trigger (370) to an opened position may reduce costs associated with components and assembly, as well as save space within the interior of casing assembly (500).

Anvil (320) is substantially like anvil (40) described above. Therefore, Anvil (320) includes a proximal shaft (324), an anvil head (328), and a pair of pivoting latch members (334); which are substantially like proximal shaft (44), anvil head (48), and pivoting latch members (30) described above, respectively. Therefore, proximal shaft (44) defines a pair of lateral openings (322) and a bore (326), which are substantially like lateral openings (42) and bore (46) described above, respectively. Anvil head (328) includes a proximal surface (330) defining a plurality of staple forming pockets (332); which are substantially like proximal surface (50) and stapling forming pockets (52) described above.

Figure 14:
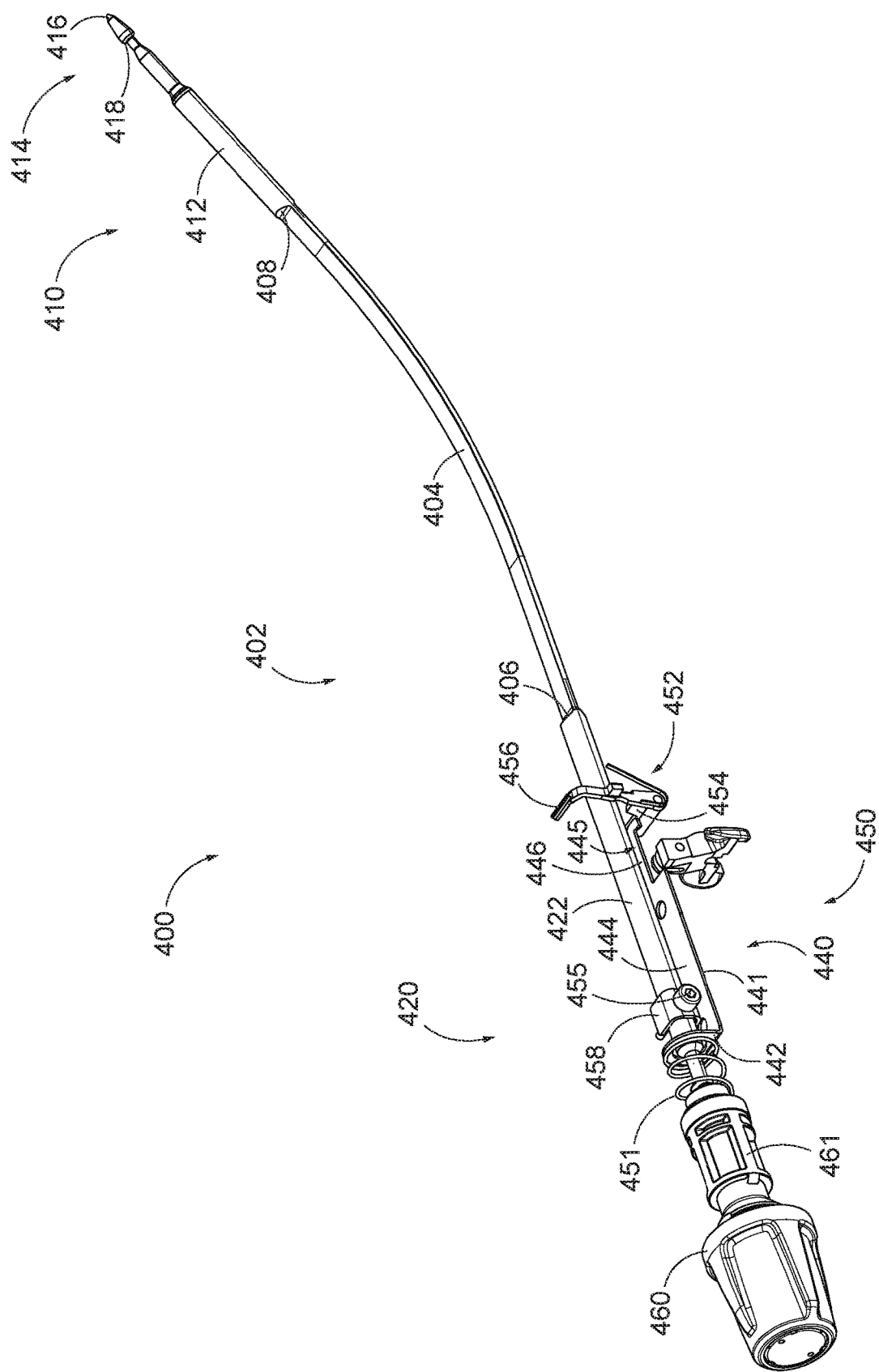
FIG. 14 depicts a perspective view of a closure system of the surgical instrument of FIG. 12.
Figure 15:
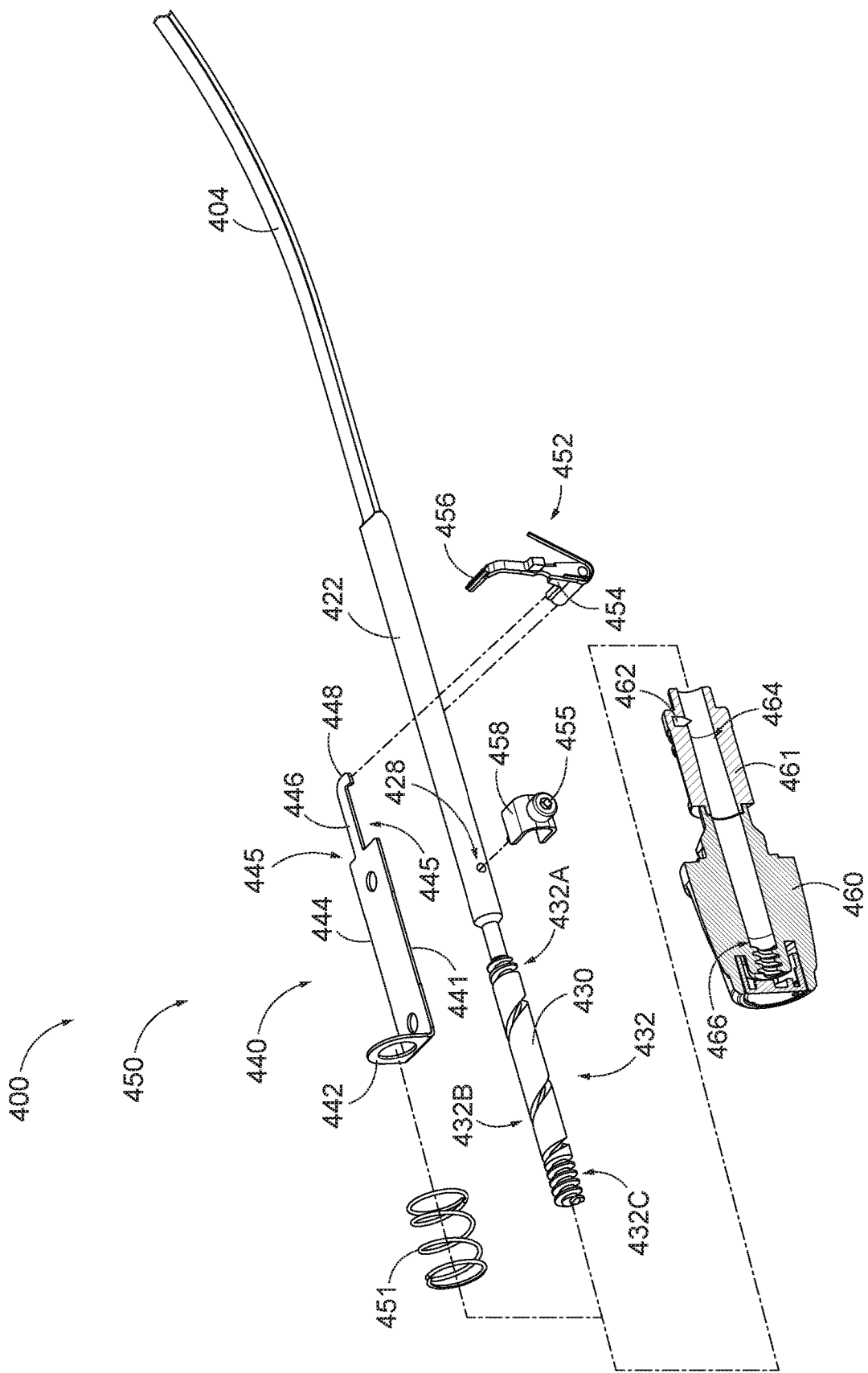
FIG. 15 depicts an exploded perspective view of the closure system of FIG. 14.

Closure system (400) is substantially like closure system described above, with differences described below. FIGS. 14-15 show closure system (400) of instrument (310). A will be described in greater detail below, closure system (400) includes a monolithic closure rod (402) extending from a proximal shank portion (420) to a distal trocar portion (410). In brief, monolithic closure rod (402) is configured to actuate relative to casing assembly (500) in response to rotation or adjustment knob (460), selectively attach to anvil (320), and actuate anvil (320) to clamp tissue between anvil (320) and deck member (364) prior to actuating firing system (360).

Closure system (400) includes monolithic closure rod (402), a gap indicator assembly (450), and an adjustment knob (460). Adjustment knob (460) is rotatably supported on a proximal end of casing assembly (500) such that adjustment knob (460) may rotate about its own longitudinal axis while remaining longitudinally stationary relative to casing assembly (500). Adjustment knob (460) includes a sleeve (461), which is substantially like sleeve (92) described above. As best seen in FIG. 15, adjustment knob (460) defines a distally open channel (464). Distally open channel (464) is dimensioned to slidably receive a proximal grooved section (430) of monolithic closure rod (402). Adjustment knob (460) includes an internal tab (462) extending within distally open channel (464) as well as an internal threading portion (466); which may be substantially similar internal tab and internal threading of adjustment knob (98) described above, respectively. Therefore, like adjustment knob (98) and grooves (96A, 96B) described above, internal tab (462) may mesh with grooves (432A, 432B) of proximal grooved section (430) such that rotation of internal tab (462) will actuate monolithic closure rod (402) relative to casing assembly (500). Additionally, like adjustment knob (98) and groove (96C) described above, internal threading (466) may selectively engage with groove (432C) when monolithic closure rod is translated proximal enough such that rotation of internal threading (466) may actuate monolithic closure rod (402) relative to casing assembly (500).

Gap indicator assembly (450) is configured to indicate through indicator window (506) a gap distance d between anvil (320) and deck member (364) during exemplary use. Gap indicator assembly (450) includes a spring (451), an indicator bracket (440), a U-shaped clip (458), and an indicator (452); which are substantially like spring (150), indicator bracket (140), U-shaped clip (100), and indicator (104) described above, respectively. Therefore, indicator bracket (140) includes an angled flange (442), a rectangular plate (444) having a surface (441), an indicator arm (446) defining gaps (445), and a laterally projecting finger (448); which are substantially like angled flange (142), rectangular plate (144) having surface (141), indicator arm (146) defining gaps (145), and laterally projecting finger (148) described above. Additionally, indicator (452) is pivotally mounted to casing assembly (500). Indicator (452) includes a tab (454), and an indicator bar (456); which are substantially like tab (106) and indicator bar (110) described above.

Like spring (150), U-shaped clip (100), and indicator bracket (140) described above, spring (451) biases angled flange (442) against U-shaped clip (458) while U-shaped clip (458) is attached to monolithic closure rod (402) via pin (455). Angled flange (442) is formed at the proximal end of rectangular plate (444) and includes an aperture to slidable mount onto monolithic closure rod (402). Therefore, as monolithic closure rod (402) is actuated distally, spring (451) will bias angled flange (442) distally to remain in engagement with U-shaped clip (458). Conversely, when monolithic closure rod (402) is actuated proximally, U-shaped clip (458) will push angled flange (442) further proximally, thereby compressing spring (451). In other words, spring (451) and U-shaped clip (458) interact with angled flange (442) such that indicator bracket (440) actuates with monolithic closure rod (402). In the present example, indicator bracket (440) is slidably attached to casing assembly (500). However, in some versions, indicator bracket (440) may be fixedly attached to monolithic closure rod (402).

In the present example, a portion of lockout feature (371) abuts a surface (441) of indicator bracket (440) when indicator bracket (440) is in a longitudinal position that does not correspond to when gap distance d is within a desired operating range (e.g., a green colored region or "green zone"). When gap distance d is within a desired operating range (e.g., a green colored region or "green zone"), indicator bracket (440) narrows to provide a pair of gaps (445) on either side of an indicator arm (446) that permits lockout feature (371) to pivot, thereby unlocking trigger (370). Accordingly, lockout feature (371) and indicator bracket (440) can substantially prevent a user from unlocking and operating trigger (370) until anvil (320) is in a predetermined operating range. Lockout feature (371) may be omitted entirely in some versions.

This operating range may be visually communicated to the user via indicator bar (456) of indicator (452) shown against a scale (not shown) of indicator window (506), described briefly above. At the distal end of indicator bracket (440) is a distally projecting indicator arm (146) which terminates at a laterally projecting finger (448) for controlling the movement of indicator (452). Indicator arm (446) and finger (448) are configured to engage tab (454) of indicator (452) such that indicator (452) is pivoted when indicator bracket (440) is actuated longitudinally. In the present example, indicator (452) is pivotably coupled to casing assembly (500) at a first end of indicator (452), though this is merely optional and other pivot points for indicator (452) will be apparent to one of ordinary skill in the art in view of the teachings herein. Indicator bar (456) is positioned on the second end of indicator (452) such that indicator bar (456) moves in response to the actuation of indicator bracket (440). Accordingly, like indicator bar (110) described above, indicator bar (456) is displayed through an indicator window (506) against a scale (not shown) to show the relative gap distance d between proximal surface (330) of anvil (320) and distally presented deck surface of deck member (364).

As best seen in FIGS. 14-15, monolithic closure rod (402) includes proximal shank portion (420), a connecting band portion (404), and distal trocar portion (410). Distal trocar portion (410) includes a shaft (412) and a head (414), which may be substantially like shaft (232) and head (234) of trocar (230) described above. Distal trocar portion (410) is slidably housed within inner core member (not shown) of tubular casing (512). Distal trocar portion (410) may interact with anvil (320) in a substantially similar manner as trocar (230) and anvil (40), described above. Head (414) includes a pointed tip (416) and an inwardly extending proximal surface (418). Shaft (412) thus provides a reduced outer diameter just proximal to head (414), with surface (418) providing a transition between the reduced outer diameter of shaft (412) and the outer diameter of head (414). While tip (416) is pointed in the present example, tip (416) is not sharp. Tip (416) will thus not easily cause trauma to tissue due to inadvertent contact with tissue. Head (414) and the distal portion of shaft (412) are configured for insertion in bore (326) of anvil (320). Proximal surface (418) and latch shelves (not shown) have complementary positions and configurations such that latch shelves (not shown) engage proximal surface (418) when proximal shaft (324) of anvil (320) is fully seated on distal trocar portion (410). Anvil (320) may thus secure to distal trocar portion (410) through a snap fitting between latch members (334) and head (414). In addition, or in the alternative, distal trocar portion (410) may include a magnetic portion (not shown) which may attract anvil (320) towards distal trocar portion (410). Still further configurations and arrangements for anvil (320) and distal trocar portion (410) will be apparent to one of ordinary skill in the art in view of the teachings herein.

Proximal shank portion (420) includes proximal grooved section (430) and a rod (422). Proximal shank portion (420) is slidably housed within handle portion (502) of casing assembly (500). Rod (422) defines a pin hole (428) that receives pin (455). As mentioned above, pin (455) couples U-shaped clip (458) of gap indicator assembly (450) to rod (422). Additionally, a portion of pin (455) may be slidably housed within a slot defined by casing assembly (500) such that rod (422), and therefore the rest of monolithic closure rod (402) is rotationally constrained about the longitudinal axis defined by monolithic closure rod (402), but also such that monolithic closure rode (402) may translate relative to casing assembly (500).

Proximal grooved section (430) of the present example comprises a continuous groove (432) formed in the outer surface of proximal grooved section (430). Accordingly, when adjustment knob (460) is rotated, internal tab (462) rides within continuous groove (432) and monolithic closure rod (402) is longitudinally actuated relative to adjustment knob (460). Rotating adjustment knob (460) in a first direction advances monolithic closure rod (402) distally relative to casing assembly (500). When distal trocar portion (410) is coupled with anvil (320), anvil (320) also advances distally relative to tubular casing (512) of casing assembly (500) thereby increasing the distance between proximal surface (330) of the anvil (320) and distally presented deck surface of deck member (364), otherwise known as gap distance d. By rotating adjustment knob (460) in the opposite direction, monolithic closure rod (402) is actuated proximally relative to casing assembly (500) to reduce the gap distance d between anvil (320) and deck member (364) when distal trocar portion (410) is coupled with anvil (320). Thus, closure system (400) is operable to actuate monolithic closure rod (402) in response to rotating adjustment knob (460). Other configurations for closure system (400) will be apparent to one of ordinary skill in the art in view of the teachings herein.

Continuous groove (432) of the present example comprises a plurality of different portions (432A, 432B, 432C) that have a varying pitch or number of grooves per axial distance. The present groove (432) is divided into a distal portion (432A), a middle portion (432B), and a proximal portion (432C). Distal portion (432A) comprises a fine pitch or a high number of grooves over a short axial length of proximal grooved section (430). Middle portion (432B) comprises a section with comparably coarser pitch or fewer grooves per axial length such that relatively few rotations are required for the internal tab (462) of adjustment knob (460) to traverse along axial distance. When anvil (320) is in an initial, distal position in relation to tubular casing (512), the internal tab (462) of knob (460) is positioned in middle portion (432B). Accordingly, the gap distance d may be quickly reduced through relatively few rotations of adjustment knob (460) while the internal tab (462) traverses middle portion (432B).

Proximal portion (432C) of the present example is substantially like distal portion (432A) and comprises a fine pitch or a high number of grooves over a short axial distance of proximal grooved section (430) such that many rotations are required to traverse the short axial distance. Proximal portion (432C) of the present example is engaged by the internal proximal threading (466) defined by knob (460) when anvil (320) is substantially near deck member (364), such that indicator bar (456) moves within indicator window (506) along scale (not shown) to indicate that the anvil gap is within a desired operating range. Accordingly, when grooved proximal grooved section (430) reaches a proximal position where the proximal portion (432C) of groove (432) engages the internal proximal threading (466) of knob (460), each rotation of adjustment knob (460) may reduce the gap distance d by a relatively small amount to provide for fine tuning.

Connecting band portion (404) extends between proximal shank portion (420) and distal trocar portion (410) to connect a distal end of rod (422) and a proximal end of shaft (412). Connecting band portion (404) is sufficiently flexible to actuate along the longitudinal profile of preformed bent shaft portion (504) of casing assembly (500).

Casing assembly (500) forms a mechanical ground for the firing system (360) and closure system (400). Casing assembly (500) includes a first portion (510) and a second portion (560) configured to couple with each other to house portions or firing system (360) and closure system (400). Unlike instrument (10), casing assembly (500) forms a handle portion (502), a preformed bent shaft portion (504), and a tubular casing (512). Similar to shaft assembly (60), preformed bent shaft portion (504) slidably houses a portion of closure system (400) and firing system (360). Unlike shaft assembly (60), preformed bent shaft portion (504) includes a preformed bend.

Like tubular casing (210) described above, tubular casing (512) also includes cylindraceous inner core member (not shown) that slidable receives a trocar portion (410) of closure system (400). When coupled together, first portion (510) and second portion (560) defines an indicator window (506) and a proximal opening (508). Similar to indicator window (120) described above, indicator window (506) has a scale (now shown) and is dimensioned such that an operator may view indicator bar (110) against scale (not shown) in order to determine gap distance d. Additionally, when coupled together, first portion (510) and second portion (560) define a proximal opening (508), which rotatably supports adjustment knob (460) of closure system (400).

B. Exemplary Firing System Having Trigger with Integrated Resilient Member

Firing system (360) is substantially like firing system described above, with differences described below. Therefore, firing system (360) includes a trigger (370), a slidable trigger carriage (367), a driver actuator (365), a slidable staple driver member (362) defining a bore (366), a cylindraceous knife member (363), and a deck member (364); which are substantially like trigger (74), slidable trigger carriage (86), driver actuator (64), slidable staple driver member (250) defining a bore (254), cylindraceous knife member (240), and deck member (220) described above, respectively, with differences described below.

As will be described in greater detail below, trigger (370) is operable to actuate slidable trigger carriage (367), driver actuator (365), slidable staple driver member (362), and cylindraceous knife member (363) to thereby simultaneously staple and sever tissue between anvil (320) and deck member (364). Like driver actuator (64) described above, driver actuator (365) comprises a tubular member having an open longitudinally extending channel such that adjacent portions of monolithic closure rod (402) may actuate longitudinally within and relative to driver actuator (365).

Slidable staple driver member (362) includes a plurality of staple drivers (368), which are substantially like staple drivers (252) described above. Deck member (364) houses a plurality of staples within staple pockets (not shown) that align with respective staple drivers (368). Staple drivers (368) are configured to drive staples from staple pockets of deck member (364), through an annular array of staple openings (not shown) of deck member (368), and against a plurality of staple forming pockets (332) of anvil (320), in accordance with the principles described above. Like cylindraceous knife member (240), cylindraceous knife member (363) is coupled with slidable staple driver member (362) to actuate with slidable staple driver member (362) to sever excess tissue radially interior to newly formed staples, in accordance with the principles described above.

FIGS. 16-19 show trigger (370) of the present example in greater detail. Trigger (370) extends from distal portion (380) to a proximal portion (382). Trigger (370) includes a lever (372) and an integral leaf spring (374) extending distally from lever (372). Lever (372) includes a pair of side walls (378) connected to each other with a bottom wall (379). Each side wall (378) includes a tab (376) and a lockout interface (386). Additionally, each side wall (378) also defines a pivot hole (375). Pivot holes (375) are dimensioned to receive a pivot boss (514) of first portion (500) of casing assembly (500), thereby pivotally coupling trigger (370) with casing assembly (500). Trigger (370) is pivotably coupled with casing assembly (500) and is configured to pivot relative to casing assembly (500) from an opened position to a closed position to actuate slidable staple driver member (362) and cylindraceous knife member (363) to staple and sever tissue captured between anvil (320) and deck member (364) during exemplary use.

Tabs (376) of the present example are operable like tabs (88) described above. Therefore, tabs (376) are configured to interact with slidable trigger carriage (367) when trigger (370) is pivoted from the opened position to the closed position in order distally actuate trigger carriage (367). Trigger carriage (367) is coupled with driver actuator (365) such that movement of trigger carriage (367) causes movement of slidable staple driver member (362), and cylindraceous knife member (363), in accordance with the principle described above.

Lockout interface (386) is dimensioned to interact with lockout features (371) such that lockout feature (371) may prevent pivoting of trigger (370), like trigger (74) and lockout feature (82) described above. Alternatively, lockout interface (386) may be dimensioned to replace lockout feature (371) all together, such that lockout interface (386) may abut against surface (441) of indicator bracket (440) to prevent accidental firing of trigger (370) when anvil (320) is not within the desired operating range (e.g., a green colored region or "green zone").

Figure 16:
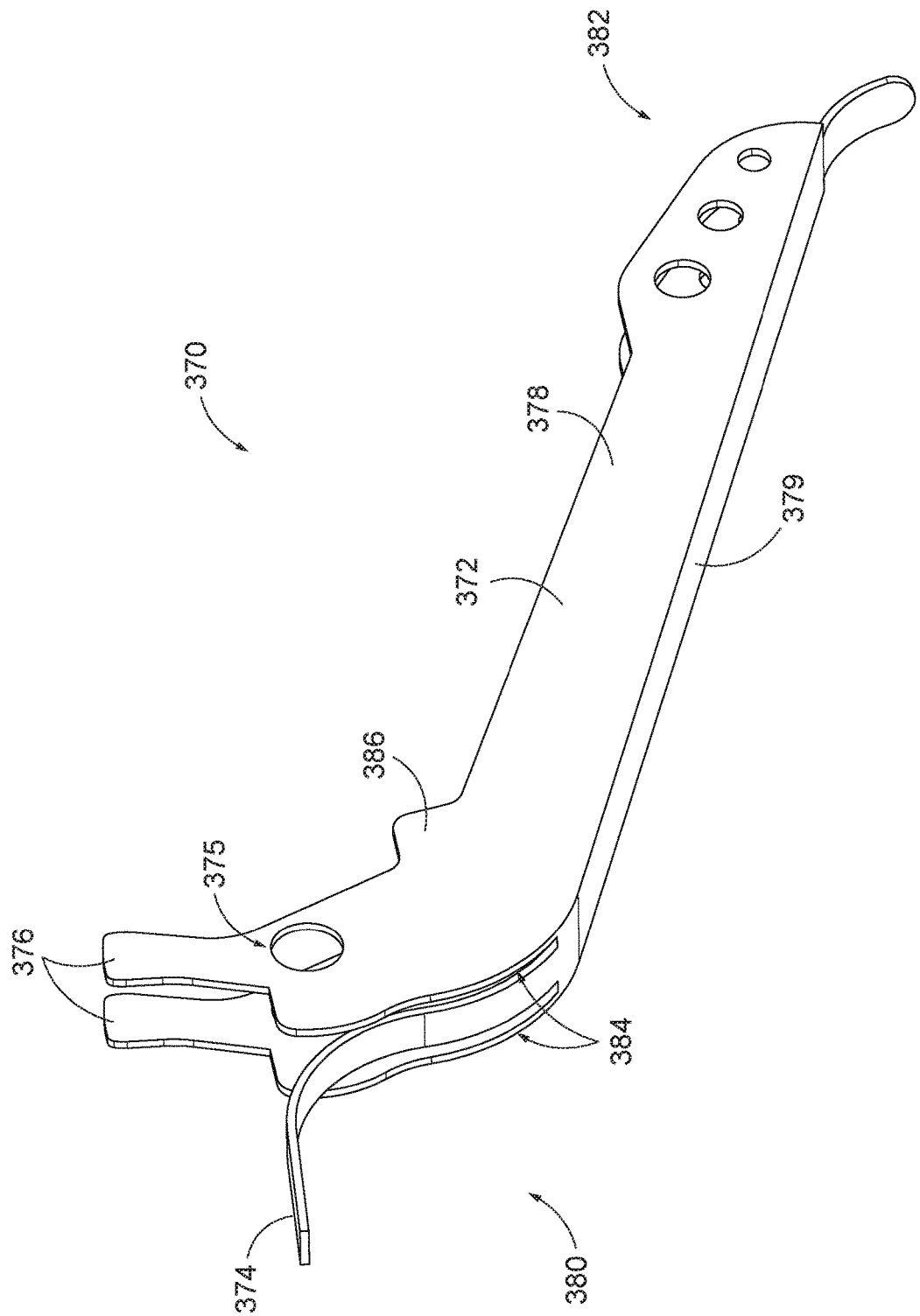
FIG. 16 depicts a perspective view of a trigger of the closure assembly of FIG. 14.
Figure 17:
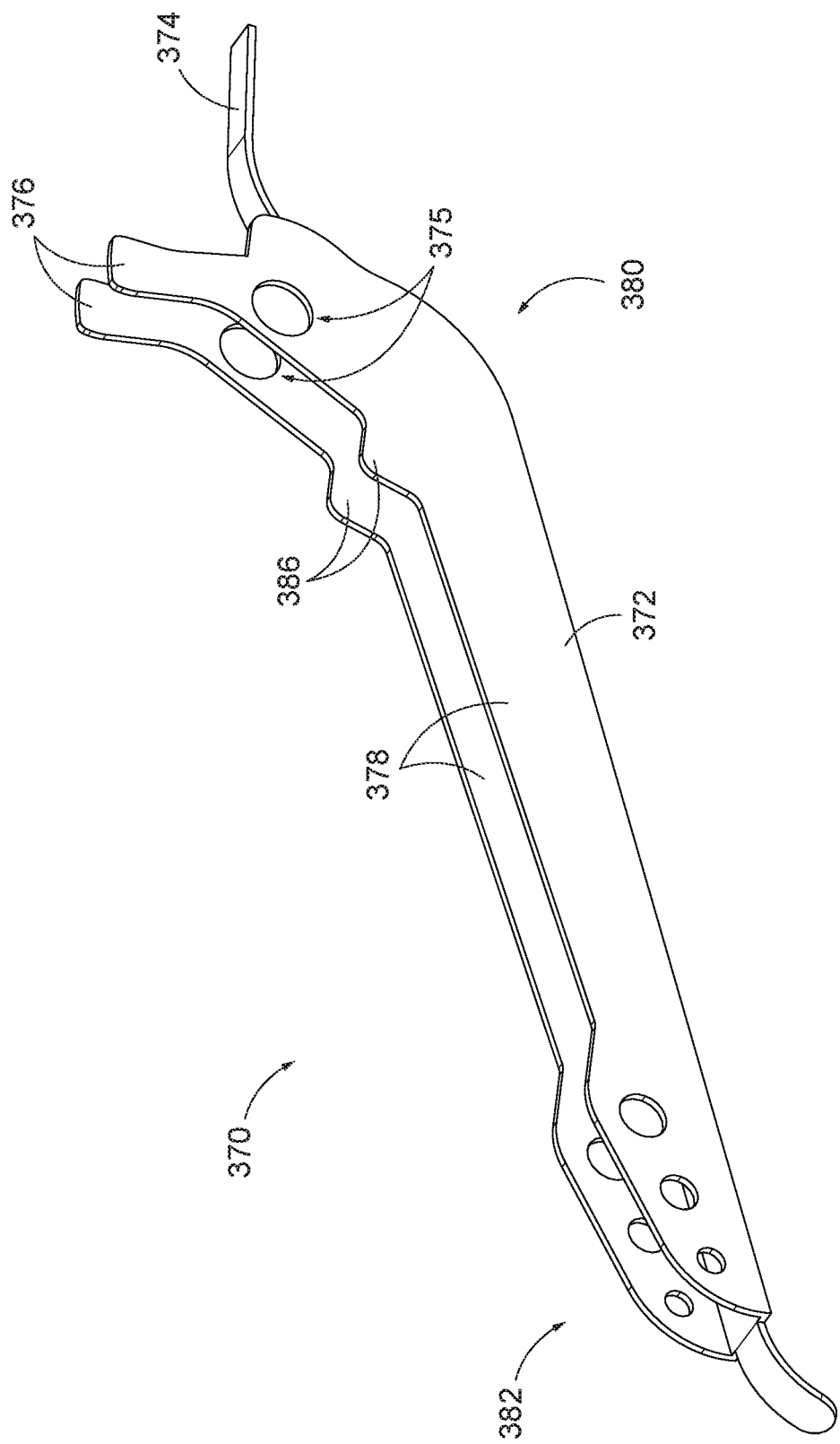
FIG. 17 depicts another perspective view of the trigger of FIG. 16.
Figure 18:
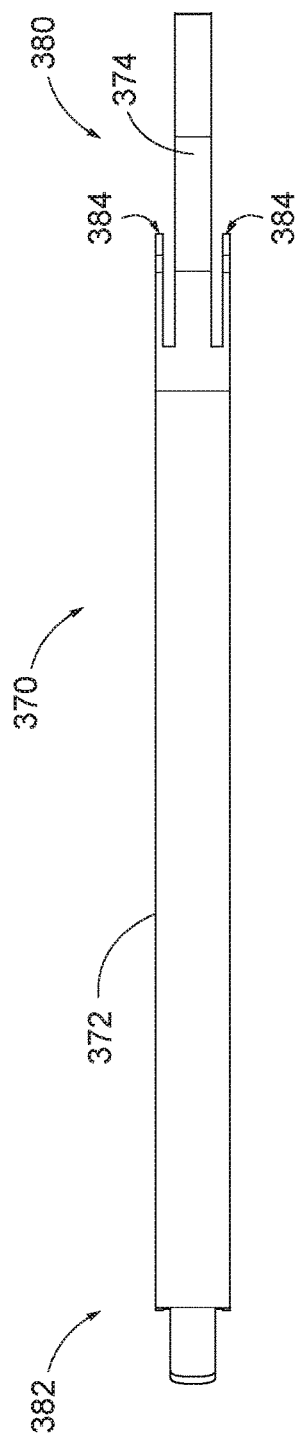
FIG. 18 depicts a bottom plan view of the trigger of FIG. 16.
Figure 19:
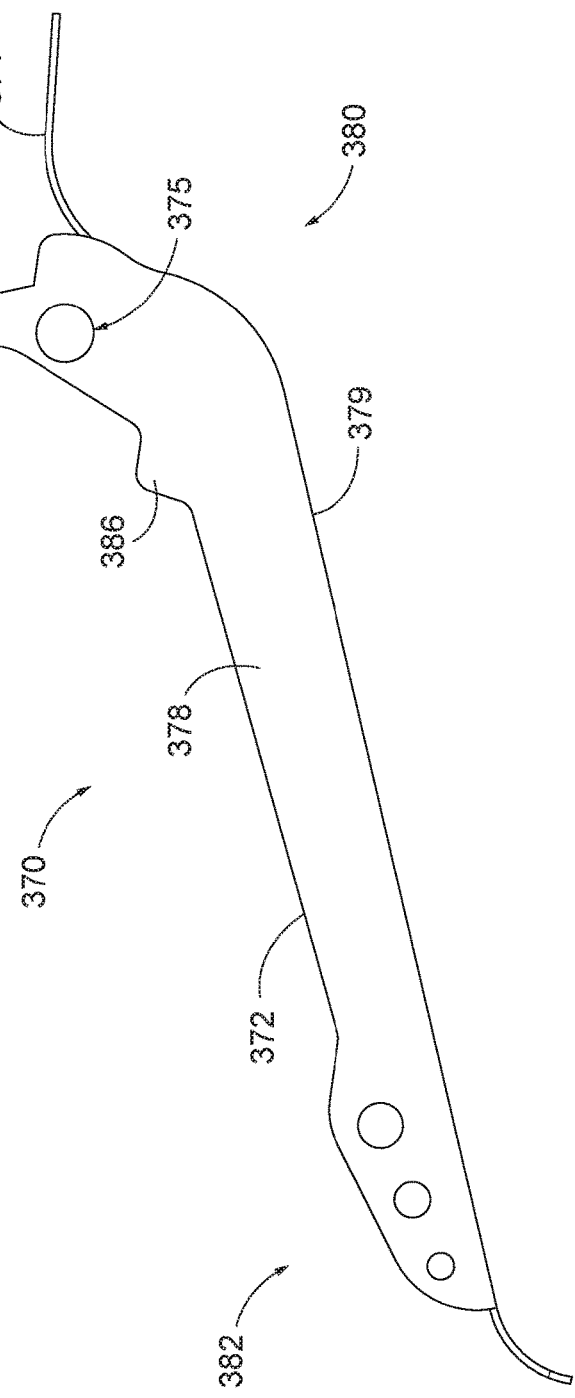
FIG. 19 depicts a side elevation view of the trigger of FIG. 16.
Figure 20:
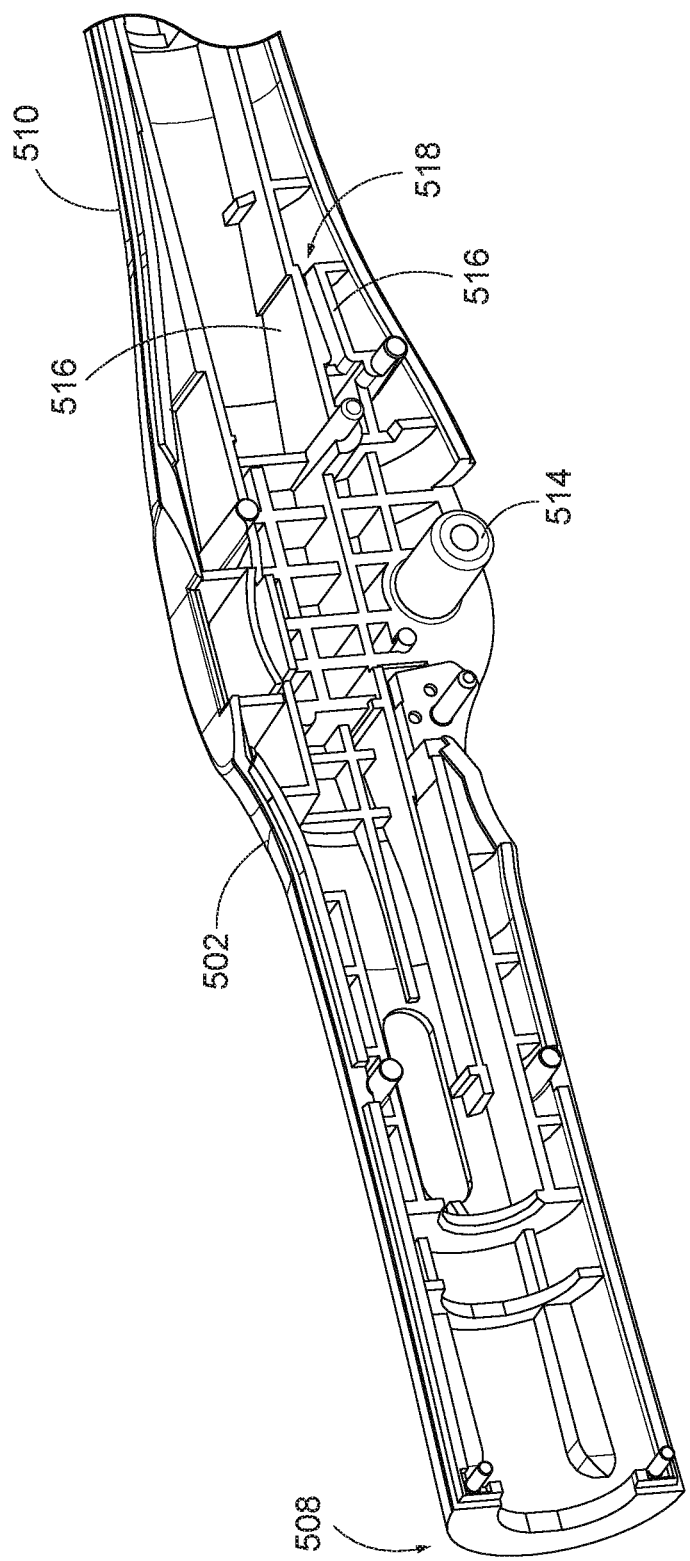
FIG. 20 depicts a perspective view of a first portion of a casing assembly of the surgical instrument of FIG. 12.

As best seen in FIGS. 16 and 18, integral leaf spring (374) extends from bottom wall (379), along the distal profile of side walls (378), and distally from the rest of trigger (370). The portion of leaf spring (374) extending along the distal profile of side walls (378) defines a respective gap (384) with each side wall (378). Therefore, leaf spring (374) has a width smaller than the lateral distance between side walls (378). This may allow leaf spring (374) to pivot and/or otherwise move relative to within the cavity defined by both side walls (378) and bottom wall (379).

Figure 21A:
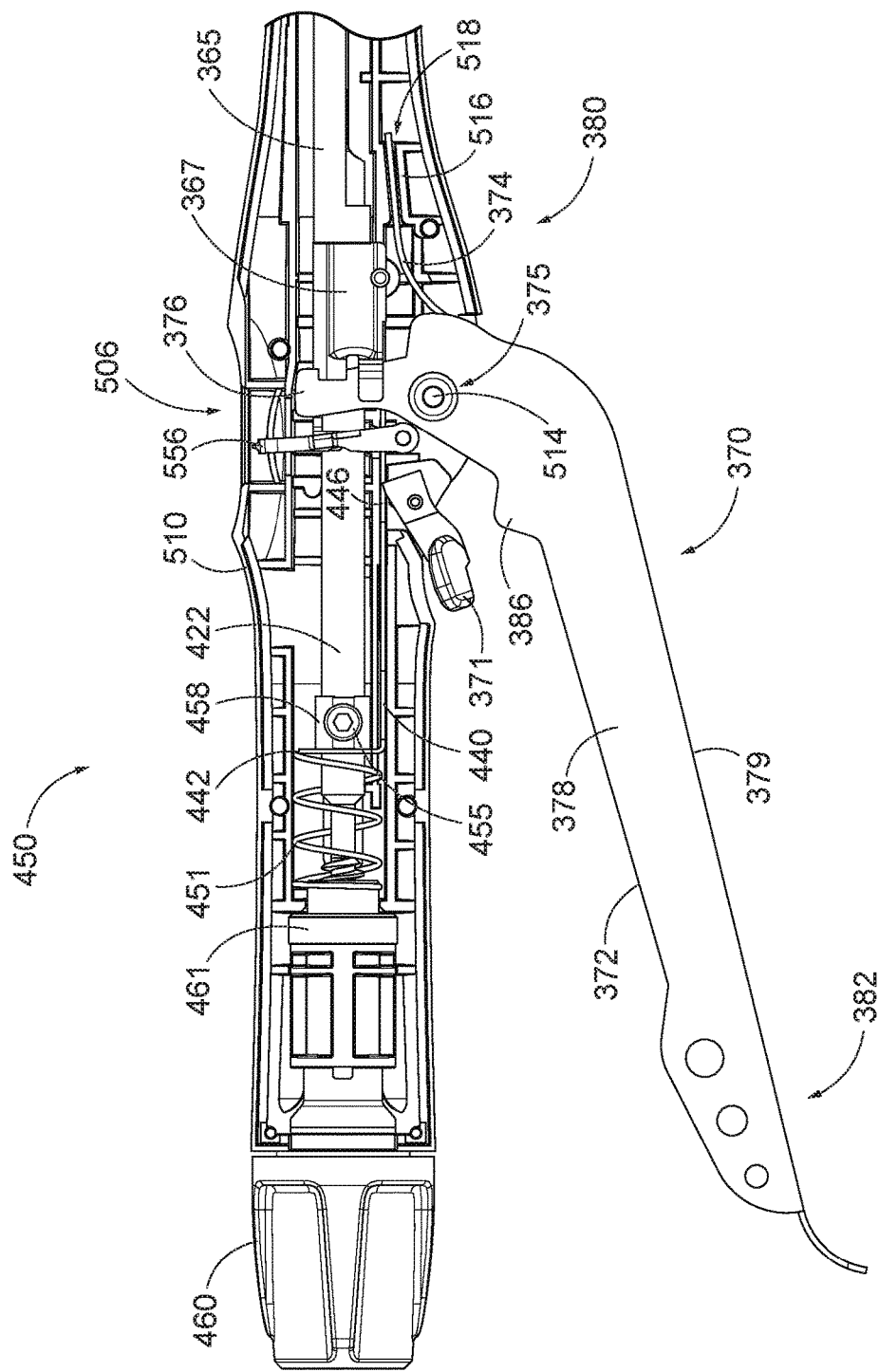
FIG. 21A depicts an enlarged side elevation view of a handle portion of the surgical instrument of FIG. 12, with a portion of the body removed, showing the trigger of FIG. 16 in an unfired position and a lockout feature in a locked position.
Figure 21B:
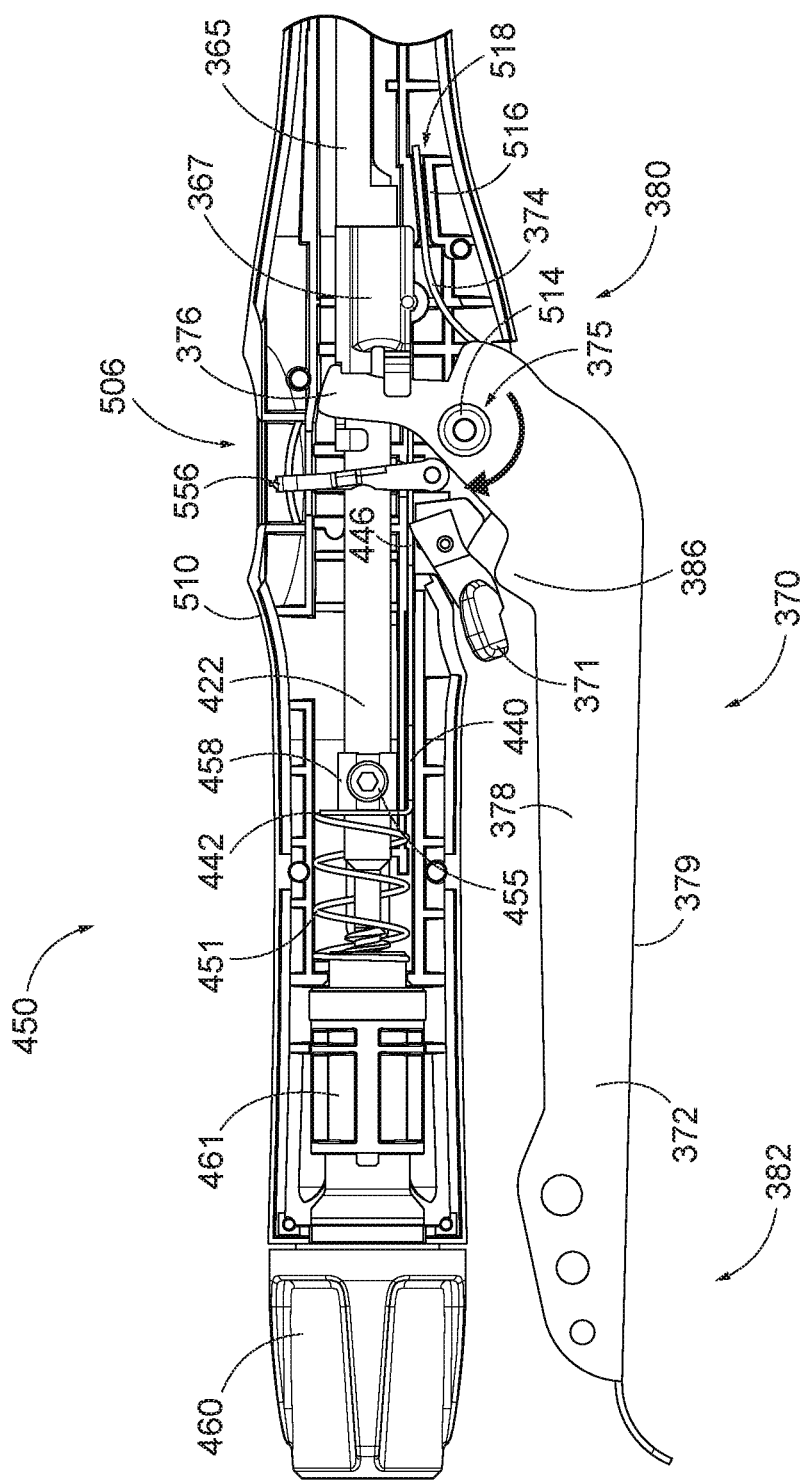
FIG. 21B depicts an enlarged side elevation view of the handle portion of FIG. 21A, with a portion of the body removed, showing the trigger in a fired position and the lockout feature in an unlocked position.
Figure 21C:
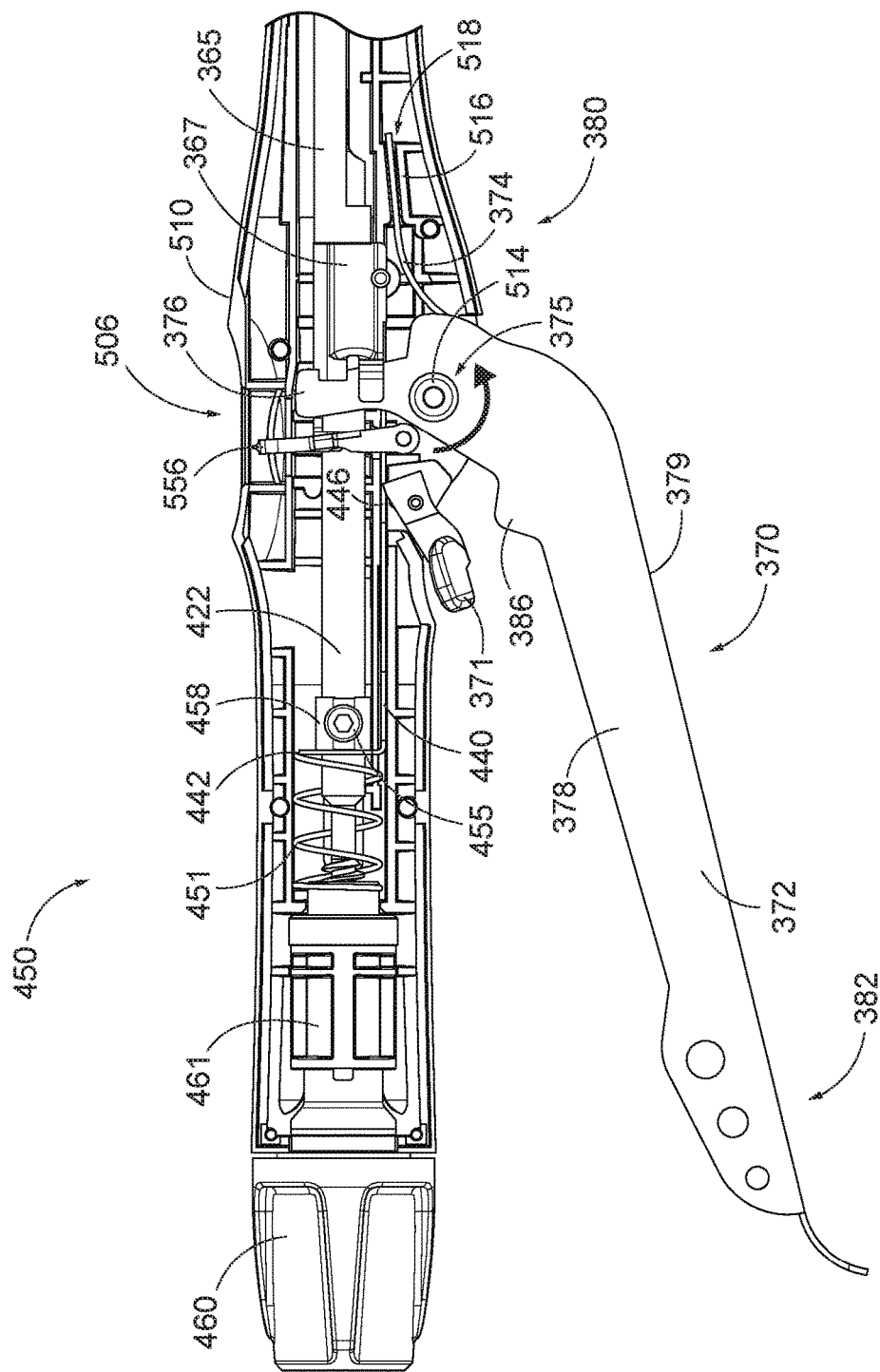
FIG. 21C depicts an enlarged side elevation view of the handle portion of FIG. 21A, with a portion of the body removed, showing the trigger biased from the fired position to the unfired position and the lockout feature in an unlocked position.

The portion of leaf spring (374) extending distally from side wall (378) is dimensioned to be housed within a spring channel (518) defined by internal ribbing (516) of handle assembly (500). Integral leaf spring (374) is sufficiently resilient and dimensioned to bias trigger (370) toward an open position. Specifically, as shown between FIGS. 21A-21C, integral leaf spring (374) may resiliently bend or flex from a natural position associated with trigger (370) in an open position (as shown in FIG. 21A), toward a flexed position associated with trigger (370) in the closed position (as shown in FIG. 21B), in response to an operator pivoting trigger (370). Once an operator releases trigger (370) (as shown in FIG. 21C), integral leaf spring (374) may resiliently return to its natural position, thereby abutting against internal ribs (516) to pivot trigger (370) back to the opened position.

Trigger (370) may be formed from a single piece of material (i.e., such that the entirety of trigger (370) consists of a homogenous continuum of material), and integral leaf spring (374) may be stamped and bent from that same single piece of material to provide the desired geometric shape relative to the rest of trigger (370). Trigger (370) may be formed with any suitable material having any suitable thickness that would be apparent to one having ordinary skill in the art in view of the teachings herein. For example, trigger (370) may be formed out of sheet metal having an initial thickness of about 0.040 inches. Because integral leaf spring (374) is formed unitarily with the rest of trigger (370), assembly may be simplified while part costs may be reduced.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus, comprising: (a) a body assembly comprising: (i) a handle portion, wherein the handle portion comprises a pivot boss and a pair of internal ribs defining a spring channel, and (ii) a shaft portion extending distally from the handle portion; (b) an end effector comprising a staple driver, wherein the staple driver is operable to actuate relative to the shaft portion of the body between an unfired position and a fired position; and (c) a firing assembly comprising: (i) a driver actuator configured to actuate the staple driver between the unfired position and the fired position, wherein the driver actuator is in communication with the staple driver, wherein the driver actuator is slidably housed within the shaft portion, and (ii) a trigger comprising a lever and an integral spring member, wherein the lever is pivotally coupled to the handle portion via the pivot boss, wherein the trigger is configured to pivot between a first position and a second position to slide the driver actuator within the shaft portion, wherein the first position is associated with the staple driver in the unfired position, wherein the second position is associated with the staple driver in the fired position, wherein the integral spring member is at least partially housed within the spring channel of the handle portion, wherein the integral spring member is configured to resiliently bias the trigger toward the first position.

EXAMPLE 2

The apparatus of Example 1, wherein the lever further comprises a first side wall defining a first pivot hole and a second side wall defining a second pivot hole, wherein the pivot boss extends through the first pivot hole and the second pivot hole.

EXAMPLE 3

The apparatus of Example 2, wherein the lever further comprises a bottom wall, wherein the integral spring member extends from the bottom wall of the lever.

EXAMPLE 4

The apparatus of any one or more of Examples 1 through 3, wherein the integral spring member comprises a leaf spring.

EXAMPLE 5

The apparatus of Example 4, wherein the lever and the integral spring member are formed from a single piece of sheet metal such that the lever and the integral spring member consist of a homogenous continuum of material.

EXAMPLE 6

The apparatus of Example 5, wherein the single piece of sheet metal has a thickness of 0.040 inches.

EXAMPLE 7

The apparatus of any one or more of Examples 1 through 6, wherein the lever comprises a pair of tabs configured to communicate motion to the driver actuator.

EXAMPLE 8

The apparatus of any one or more of Examples 1 through 7, further comprising an anvil and a closure system, wherein the closure system is configured to selectively couple with the anvil and actuate the anvil relative to the end effector.

EXAMPLE 9

The apparatus of Example 8, wherein the closure system further comprises a gap indicator assembly, wherein the gap indicator assembly is configured to prevent the trigger from pivoting to the second position when the anvil is out of a predetermined operating range relative to the end effector, wherein the gap indicator assembly is configured to allow the trigger to pivot to the second position when the anvil is within the predetermined operating range relative to the end effector.

EXAMPLE 10

The apparatus of Example 9, wherein the gap indicator assembly comprises an indicator bracket within the handle assembly, wherein the trigger comprises a lockout interface, wherein the indicator bracket in configured to directly abut against the lockout interface when the anvil is out of the predetermined operating range relative to the end effector.

EXAMPLE 11

The apparatus of any one or more of Examples 8 through 10, wherein the closure system further comprises a rotary knob attached to the body assembly and a trocar slidably housed within the body assembly, wherein the rotary knob is configured to rotate in order to slide the trocar relative to the body assembly.

EXAMPLE 12

The apparatus of any one or more of Examples 1 through 11, wherein the integral spring extends distally relative to the lever.

EXAMPLE 13

The apparatus of any one or more of Examples 1 through 12, wherein the end effector further comprises a cylindrical knife member coupled with the staple driver.

EXAMPLE 14

The apparatus of any one or more of Examples 1 through 13, further comprising an slidable trigger carriage attached to the trigger and the driver actuator.

EXAMPLE 15

The apparatus of any one or more of Examples 1 through 14, wherein the shaft portion comprises a pre-formed bend.

EXAMPLE 16

An apparatus, comprising: (a) a body assembly comprising a handle portion; (b) an end effector comprising a staple driver, wherein the staple driver is operable to actuate relative to the body assembly between an unfired position and a fired position; and (c) a trigger comprising a lever and an integral spring member extending unitarily from the lever, wherein the lever is pivotally coupled to the handle portion, wherein the trigger is configured to pivot between a first position and a second position to slidably actuate the staple driver, wherein the first position is associated with the staple driver in the unfired position, wherein the second position is associated with the staple driver in the fired position, wherein the integral spring member is housed within the body assembly, wherein the integral spring member is configured to resiliently bias the trigger relative to the body assembly toward the first position.

EXAMPLE 17

The apparatus of Example 16, wherein the lever comprises a first side wall and a second side wall defining a gap, wherein the integral spring member has a first portion extending within the gap of the first side wall and the second side wall.

EXAMPLE 18

The apparatus of Example 17, wherein the integral spring comprise a second portion that abuts against an internal rib of the body assembly.

EXAMPLE 19

An apparatus, comprising: (a) a body assembly comprising: (i) a handle portion, (ii) a shaft portion extending distally from the handle portion; (b) an end effector comprising a staple driver, wherein the staple driver is operable to actuate relative to the shaft portion of the body between an unfired position and a fired position; and (c) a trigger configured to pivot between a first position and a second position to actuate the staple driver, wherein the first position is associated with the staple driver in the unfired position, wherein the second position is associated with the staple driver in the fired position wherein the trigger is made from a single piece of sheet metal such that the trigger consists of a homogenous continuum of material, wherein the trigger comprises: (i) a lever pivotally coupled to the handle portion, and (ii) an integral spring member, wherein the integral spring member is configured to resiliently bias the trigger toward the first position.

EXAMPLE 20

The apparatus of Example 19, wherein the handle portion of the body assembly houses a portion of the integral spring member.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. patent application Ser. No. 13/693,430, entitled "Trans-Oral Circular Anvil Introduction System with Dilation Feature," filed Dec. 4, 2012, issued as U.S. Pat. No. 9,572,573 on Feb. 21, 2017, the disclosure of which is incorporated by reference herein; U.S. patent application Ser. No. 13/688,951, entitled "Surgical Staple with Integral Pledget for Tip Deflection," filed Nov. 29, 2012, issued as U.S. Pat. No. 9,289,207 on Mar. 22, 2016, the disclosure of which is incorporated by reference herein; U.S. patent application Ser. No. 13/706,827, entitled "Surgical Stapler with Varying Staple Widths along Different Circumferences," filed Dec. 6, 2012, now abandoned, the disclosure of which is incorporated by reference herein; U.S. patent application Ser. No. 13/688,992, entitled "Pivoting Anvil for Surgical Circular Stapler," filed Nov. 29, 2012, issued as U.S. PAt. No. 9,498,222 on Nov. 22, 2016, the disclosure of which is incorporated by reference herein; U.S. patent application Ser. No. 13/693,455, entitled "Circular Anvil Introduction System with Alignment Feature," filed Dec. 4, 2012, issued as U.S. Pat. No. 9,724,100 on Aug. 8, 2017, the disclosure of which is incorporated by reference herein; U.S. patent application Ser. No. 13/716,313, entitled "Circular Stapler with Selectable Motorized and Manual Control, Including a Control Ring," filed Dec. 17, 2012, issued as U.S. Pat. No. 9,532,783 on Jan. 3, 2017, the disclosure of which is incorporated by reference herein; U.S. patent application Ser. No. 13/716,318, entitled "Motor Driven Rotary Input Circular Stapler with Modular End Effector," filed Dec. 17, 2012, issued as U.S. Pat. No. 9,597,081 on MAr. 21, 2017, the disclosure of which is incorporated by reference herein; and/or U.S. patent application Ser. No. 13/716,323, entitled "Motor Driven Rotary Input Circular Stapler with Lockable Flexible Shaft," filed Dec. 17, 2012, issued as U.S. Pat. No. 9,463,022 on Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body assembly comprising:
      (i) a handle portion, wherein the handle portion comprises a pivot boss and a pair of internal ribs defining a spring channel, and
      (ii) a shaft portion extending distally from the handle portion;
   (b) an end effector comprising a staple driver, wherein the staple driver is operable to actuate relative to the shaft portion of the body between an unfired position and a fired position; and
   (c) a firing assembly comprising:
      (i) a driver actuator configured to actuate the staple driver between the unfired position and the fired position, wherein the driver actuator is in communication with the staple driver, wherein the driver actuator is slidably housed within the shaft portion, and
      (ii) a trigger comprising a lever and an integral spring member, wherein the lever is pivotally coupled to the handle portion via the pivot boss, wherein the trigger is configured to pivot between a first position and a second position to slide the driver actuator within the shaft portion, wherein the first position is associated with the staple driver in the unfired position, wherein the second position is associated with the staple driver in the fired position, wherein the integral spring member comprises a proximal portion coupled to the lever and a distal portion terminating into a free end, wherein the distal portion of the integral spring member is at least partially housed within the spring channel of the handle portion, wherein the integral spring member is configured to resiliently bias the trigger toward the first position.

2. The apparatus of claim 1, wherein the lever further comprises a first side wall defining a first pivot hole and a second side wall defining a second pivot hole, wherein the pivot boss extends through the first pivot hole and the second pivot hole.

3. The apparatus of claim 2, wherein the lever further comprises a bottom wall, wherein the integral spring member extends from the bottom wall of the lever.

4. The apparatus of claim 1, wherein the integral spring member comprises a leaf spring.

5. The apparatus of claim 4, wherein the lever and the integral spring member are formed from a single piece of sheet metal such that the lever and the integral spring member consist of a homogenous continuum of material.

6. The apparatus of claim 5, wherein the single piece of sheet metal has a thickness of 0.040 inches.

7. The apparatus of claim 1, wherein the lever comprises a pair of tabs configured to communicate motion to the driver actuator.

8. The apparatus of claim 1, further comprising an anvil and a closure system, wherein the closure system is configured to selectively couple with the anvil and actuate the anvil relative to the end effector.

9. The apparatus of claim 8, wherein the closure system further comprises a gap indicator assembly, wherein the gap indicator assembly is configured to prevent the trigger from pivoting to the second position when the anvil is out of a predetermined operating range relative to the end effector, wherein the gap indicator assembly is configured to allow the trigger to pivot to the second position when the anvil is within the predetermined operating range relative to the end effector.

10. The apparatus of claim 9, wherein the gap indicator assembly comprises an indicator bracket within the handle assembly, wherein the trigger comprises a lockout interface, wherein the indicator bracket in configured to directly abut against the lockout interface when the anvil is out of the predetermined operating range relative to the end effector.

11. The apparatus of claim 8, wherein the closure system further comprises a rotary knob attached to the body assembly and a trocar slidably housed within the body assembly, wherein the rotary knob is configured to rotate in order to slide the trocar relative to the body assembly.

12. The apparatus of claim 1, wherein the integral spring extends distally relative to the lever.

13. The apparatus of claim 1, wherein the end effector further comprises a cylindrical knife member coupled with the staple driver.

14. The apparatus of claim 1, further comprising a slidable trigger carriage attached to the trigger and the driver actuator.

15. The apparatus of claim 1, wherein the shaft portion comprises a pre-formed bend.

16. An apparatus, comprising:
   (a) a body assembly comprising a handle portion;
   (b) an end effector comprising a staple driver, wherein the staple driver is operable to actuate relative to the body assembly between an unfired position and a fired position; and
   (c) a trigger comprising a lever and an integral spring member extending unitarily from the lever, wherein the lever is pivotally coupled to the handle portion, wherein the trigger is configured to pivot between a first position and a second position to slidably actuate the staple driver, wherein the first position is associated with the staple driver in the unfired position, wherein the second position is associated with the staple driver in the fired position, wherein the integral spring member is housed within the body assembly, wherein the integral spring member is configured to resiliently bias the trigger relative to the body assembly toward the first position, wherein the integral spring member extends distally past the lever.

17. The apparatus of claim 16, wherein the lever comprises a first side wall and a second side wall defining a gap, wherein the integral spring member has a first portion extending within the gap of the first side wall and the second side wall.

18. The apparatus of claim 17, wherein the integral spring comprise a second portion that abuts against an internal rib of the body assembly.

19. An apparatus, comprising:
   (a) a body assembly comprising:
      (i) a handle portion,
      (ii) a shaft portion extending distally from the handle portion;
   (b) an end effector comprising a staple driver, wherein the staple driver is operable to actuate relative to the shaft portion of the body between an unfired position and a fired position; and
   (c) a trigger configured to pivot between a first position and a second position to actuate the staple driver, wherein the first position is associated with the staple driver in the unfired position, wherein the second position is associated with the staple driver in the fired position wherein the trigger is made from a single piece of sheet metal such that the trigger consists of a homogenous continuum of material, wherein the trigger comprises:
      (i) a lever pivotally coupled to the handle portion, wherein the lever comprises a first side wall, a second side wall, and a bottom wall extending between the first side wall and the second side wall, and
      (ii) an integral spring member, wherein the integral spring member is configured to resiliently bias the trigger toward the first position, wherein the integral spring member extends between a proximal portion and a distal end, wherein the proximal portion of the integral spring member is coupled to the bottom wall, wherein the proximal portion of the integral spring member defines a gap with both the first side wall and the second side wall.

20. The apparatus of claim 19, wherein the handle portion of the body assembly houses a portion of the integral spring member.

* * * * *